United States Patent
Al-Shamkhani et al.

(10) Patent No.: US 11,001,638 B2
(45) Date of Patent: May 11, 2021

(54) IMMUNOMODULATORY ANTIBODIES

(71) Applicant: Cancer Research Technology Limited, London (GB)

(72) Inventors: Aymen Al-Shamkhani, Southampton (GB); Hak Tak Claude Chan, Southampton (GB); Mark Steven Cragg, Southampton (GB); Ruth Rosemary French, Southampton (GB); Martin John Glennie, Southampton (GB); Jane Elizabeth Willoughby, Southampton (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 15/773,821

(22) PCT Filed: Nov. 4, 2016

(86) PCT No.: PCT/EP2016/076747
§ 371 (c)(1),
(2) Date: May 4, 2018

(87) PCT Pub. No.: WO2017/077085
PCT Pub. Date: May 11, 2017

(65) Prior Publication Data
US 2018/0327504 A1 Nov. 15, 2018
US 2020/0017594 A9 Jan. 16, 2020

(30) Foreign Application Priority Data
Nov. 4, 2015 (GB) ..................... 1519481

(51) Int. Cl.
C07K 16/28 (2006.01)
A61K 39/395 (2006.01)
A61P 35/02 (2006.01)
A61K 39/00 (2006.01)
A61K 45/06 (2006.01)

(52) U.S. Cl.
CPC ...... *C07K 16/2878* (2013.01); *A61K 39/0011* (2013.01); *A61K 39/3955* (2013.01); *A61K 39/39558* (2013.01); *A61K 45/06* (2013.01); *A61P 35/02* (2018.01); *C07K 16/2818* (2013.01); *A61K 2039/505* (2013.01); *A61K 2039/507* (2013.01); *A61K 2039/545* (2013.01); *A61K 2039/57* (2013.01); *A61K 2039/575* (2013.01); *A61K 2039/80* (2018.08); *C07K 2317/24* (2013.01); *C07K 2317/52* (2013.01); *C07K 2317/53* (2013.01); *C07K 2317/565* (2013.01); *C07K 2317/567* (2013.01); *C07K 2317/75* (2013.01)

(58) Field of Classification Search
None
See application file for complete search history.

(56) References Cited

U.S. PATENT DOCUMENTS

2009/0068192 A1† 3/2009 Jure-Kunkel

FOREIGN PATENT DOCUMENTS

| EP | 3371219 | 9/2018 |
|---|---|---|
| EP | 16794556.7 | 1/2020 |
| WO | WO 2003/083069 A2 | 10/2003 |
| WO | 2005035584 A1 † | 4/2005 |
| WO | WO 2012/032433 A1 | 3/2012 |
| WO | WO 2014/148895 * | 9/2014 |
| WO | WO 2014/148895 A1 | 9/2014 |
| WO | WO 2016/185016 A1 | 11/2016 |
| WO | PCT/EP2016/076747 | 5/2017 |
| WO | PCT/EP2016/076747 | 5/2018 |

OTHER PUBLICATIONS

Munks et al., 4-1BB and OX40 stimulation enhance CD8 and CD4 T-cell responses to a DNA prime, poxvirus boost vaccine. Immunology. Aug. 2004;112(4):559-66.
European Examination Report for Application No. EP 16794556.7, dated Jan. 2, 2020.
Urelumab, p. 1.†
S. Michael Chin et al., Structure of the 4-1BB/4-1BBL complex and distinct binding and functional properties of utomilumab and urelumab, 13 pages, Nov. 8, 2018.†
Urelumab, 1 page.†
Shi-Yan Li et al., Immunotherapy of melanoma with the immune costimulatory monoclonal antibodies targeting CD137, 7 pages, Aug. 30, 2013, Dovepress.†

\* cited by examiner
† cited by third party

Primary Examiner — Laura B Goddard
(74) Attorney, Agent, or Firm — Wolf, Greenfield & Sacks, P.C.

(57) ABSTRACT

The invention relates to antibodies specific for 4-1BB and OX40, as well as to methods for using such antibodies and therapeutic uses thereof.

4 Claims, 12 Drawing Sheets

Specification includes a Sequence Listing.

C

| mAb | | Stimulatory | Inhibitory |
|---|---|---|---|
| SAP$_{4\text{-}1BB}$3-28 | m1 | - | - |
| SAP$_{OX40}$29-50 | m1 | +++ | |
| SAP$_{OX40}$25-29 | m1 | ++ | |
| SAP$_{OX40}$29-50 | m2a | - | ?/+ |
| SAP$_{OX40}$15-3 | m1 | +++ | |
| SAP$_{OX40}$28-2 | m1 | + | |
| SAP$_{OX40}$15-4 | m1 | +++ | |
| SAP$_{OX40}$22-5 | m1 | +++ | |
| SAP$_{OX40}$25-3 | m1 | +++ | |
| SAP$_{OX40}$28-3 | m1 | + | |
| SAP$_{OX40}$29-23 | m2a | - | ?/+ |
| SAP$_{OX40}$29-23 | m1 | +++ | |
| SAP$_{OX40}$9 | m2a | - | ?/+ |
| SAP$_{OX40}$9 | m1 | ++ | |

SEQUENCE LISTING

<160> NUMBER OF SEQ ID NOS: 60

<210> SEQ ID NO 1
<211> LENGTH: 5
<212> TYPE: PRT
<213> ORGANISM: Artificial Sequence
<220> FEATURE:
<223> OTHER INFORMATION: Humanised CDR

<400> SEQUENCE: 1

Ser Tyr Gly Val His
1               5

<210> SEQ ID NO 2
<211> LENGTH: 8
<212> TYPE: PRT
<213> ORGANISM: Artificial Sequence
<220> FEATURE:
<223> OTHER INFORMATION: Humanised CDR

<400> SEQUENCE: 2

Val Ile Trp Ser Gly Gly Ile Thr
1               5

<210> SEQ ID NO 3
<211> LENGTH: 16
<212> TYPE: PRT
<213> ORGANISM: Artificial Sequence
<220> FEATURE:
<223> OTHER INFORMATION: Humanised CDR

<400> SEQUENCE: 3

Asn Gly Arg Ile Gly Ser Thr Met Thr Leu Tyr Tyr Ala Met Asp Tyr
1               5                   10                  15

```
<210> SEQ ID NO 4
<211> LENGTH: 16
<212> TYPE: PRT
<213> ORGANISM: Artificial Sequence
<220> FEATURE:
<223> OTHER INFORMATION: Humanised CDR

<400> SEQUENCE: 4

Arg Ser Ser Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Humanised CDR

<400> SEQUENCE: 5

Gln Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Humanised CDR

<400> SEQUENCE: 6

Ala Gln Asn Leu Glu Leu Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: humanised CDR

<400> SEQUENCE: 7

Asn Tyr Gly Val His
1               5

<210> SEQ ID NO 8
<211> LENGTH: 8
<212> TYPE: PRT
<213> ORGANISM: Artificial Sequence
<220> FEATURE:
<223> OTHER INFORMATION: humanised CDR

<400> SEQUENCE: 8

Val Ile Trp Ser Gly Gly Ser Thr
1               5

<210> SEQ ID NO 9
<211> LENGTH: 10
<212> TYPE: PRT
<213> ORGANISM: Artificial Sequence
<220> FEATURE:
<223> OTHER INFORMATION: humanised CDR

<400> SEQUENCE: 9

Asn Pro Tyr Tyr Arg Val Phe Met Asp Tyr
1               5                   10
```

```
<210> SEQ ID NO 10
<211> LENGTH: 15
<212> TYPE: PRT
<213> ORGANISM: Artificial Sequence
<220> FEATURE:
<223> OTHER INFORMATION: humanised CDR

<400> SEQUENCE: 10

Arg Ala Ser Glu Ser Val Asp Ser Tyr Gly Asn Ser Phe Met His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: humanised CDR

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: humanised CDR

<400> SEQUENCE: 12

Gln Gln Ser Asn Glu Asp Pro Phe Thr
1               5

<210> SEQ ID NO 13
<211> LENGTH: 5
<212> TYPE: PRT
<213> ORGANISM: Artificial Sequence
<220> FEATURE:
<223> OTHER INFORMATION: humanised CDR

<400> SEQUENCE: 13

Ser Tyr Gly Val His
1               5

<210> SEQ ID NO 14
<211> LENGTH: 8
<212> TYPE: PRT
<213> ORGANISM: Artificial Sequence
<220> FEATURE:
<223> OTHER INFORMATION: humanised CDR

<400> SEQUENCE: 14

Val Ile Trp Arg Gly Gly Ser Thr
1               5

<210> SEQ ID NO 15
<211> LENGTH: 11
<212> TYPE: PRT
<213> ORGANISM: Artificial Sequence
<220> FEATURE:
<223> OTHER INFORMATION: humanised CDR

<400> SEQUENCE: 15

Pro Leu Gly Thr Ser Trp Asp Ala Met Asp Tyr
1               5                   10
```

```
<210> SEQ ID NO 16
<211> LENGTH: 11
<212> TYPE: PRT
<213> ORGANISM: Artificial Sequence
<220> FEATURE:
<223> OTHER INFORMATION: humanised CDR

<400> SEQUENCE: 16

Arg Ala Ser Gln Asp Ile Ser Asn Tyr Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: humanised CDR

<400> SEQUENCE: 17

Tyr Lys Ser Arg Leu His Ser
1               5

<210> SEQ ID NO 18
<211> LENGTH: 9
<212> TYPE: PRT
<213> ORGANISM: Artificial Sequence
<220> FEATURE:
<223> OTHER INFORMATION: humanised CDR

<400> SEQUENCE: 18

Gln Gln Gly Asn Thr Leu Pro Tyr Thr
1               5

<210> SEQ ID NO 19
<211> LENGTH: 10
<212> TYPE: PRT
<213> ORGANISM: Artificial Sequence
<220> FEATURE:
<223> OTHER INFORMATION: humanised CDR

<400> SEQUENCE: 19

Gly Phe Ser Leu Thr Ser Tyr Gly Val His
1               5                   10

<210> SEQ ID NO 20
<211> LENGTH: 16
<212> TYPE: PRT
<213> ORGANISM: Artificial Sequence
<220> FEATURE:
<223> OTHER INFORMATION: humanised CDR

<400> SEQUENCE: 20

Val Ile Trp Ala Gly Gly Ser Thr Asn Tyr Asn Ser Ala Leu Met Ser
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: humanised CDR

<400> SEQUENCE: 21

Val Arg Glu Asp Asp Pro Tyr
1               5

<210> SEQ ID NO 22
```

<211> LENGTH: 11
<212> TYPE: PRT
<213> ORGANISM: Artificial Sequence
<220> FEATURE:
<223> OTHER INFORMATION: humanised CDR

<400> SEQUENCE: 22

Arg Ala Ser Gln Asp Ile Ser Asn Tyr Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: humanised CDR

<400> SEQUENCE: 23

Tyr Thr Ser Arg Leu His Ser
1               5

<210> SEQ ID NO 24
<211> LENGTH: 8
<212> TYPE: PRT
<213> ORGANISM: Artificial Sequence
<220> FEATURE:
<223> OTHER INFORMATION: humanised CDR

<400> SEQUENCE: 24

Gln Gln Gly Asn Thr Leu Pro Phe
1               5

<210> SEQ ID NO 25
<211> LENGTH: 10
<212> TYPE: PRT
<213> ORGANISM: Artificial Sequence
<220> FEATURE:
<223> OTHER INFORMATION: humanised CDR

<400> SEQUENCE: 25

Gly Phe Thr Phe Ser Ser Ser Tyr Ile Ser
1               5                   10

<210> SEQ ID NO 26
<211> LENGTH: 17
<212> TYPE: PRT
<213> ORGANISM: Artificial Sequence
<220> FEATURE:
<223> OTHER INFORMATION: humanised CDR

<400> SEQUENCE: 26

Trp Ile Tyr Ala Gly Thr Gly Gly Thr Ser Tyr Asn Gln Lys Phe Thr
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: humanised CDR

<400> SEQUENCE: 27

Ala Arg His Asp Tyr Asp Trp Phe Ala Tyr
1               5                   10

```
<210> SEQ ID NO 28
<211> LENGTH: 12
<212> TYPE: PRT
<213> ORGANISM: Artificial Sequence
<220> FEATURE:
<223> OTHER INFORMATION: humanised CDR

<400> SEQUENCE: 28

Arg Ala Ser Ser Ser Val Ser Ser Tyr Leu His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: humanised CDR

<400> SEQUENCE: 29

Ser Thr Ser Asn Leu Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: humanised CDR

<400> SEQUENCE: 30

Gln Gln Tyr Ser Gly Tyr Pro Tyr Thr
1               5

<210> SEQ ID NO 31
<211> LENGTH: 12
<212> TYPE: PRT
<213> ORGANISM: Artificial Sequence
<220> FEATURE:
<223> OTHER INFORMATION: humanised CDR

<400> SEQUENCE: 31

Gly Phe Ser Leu Ser Thr Ser Gly Lys Gly Val Thr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: humanised CDR

<400> SEQUENCE: 32

Thr Ile Trp Trp Asp Asp Asp Asn Arg Tyr Asn Pro Ser Leu Lys Ser
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: humanised CDR

<400> SEQUENCE: 33

Val Gln Ser Asp Trp Asp Gly Ala Met Asp Tyr
1               5                   10

<210> SEQ ID NO 34
```

```
<211> LENGTH: 10
<212> TYPE: PRT
<213> ORGANISM: Artificial Sequence
<220> FEATURE:
<223> OTHER INFORMATION: humanised CDR

<400> SEQUENCE: 34

Arg Ala Ser Ser Ser Val Ser Tyr Ile His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: humanised CDR

<400> SEQUENCE: 35

Ala Thr Ser Asn Leu Ala Ser
1               5

<210> SEQ ID NO 36
<211> LENGTH: 8
<212> TYPE: PRT
<213> ORGANISM: Artificial Sequence
<220> FEATURE:
<223> OTHER INFORMATION: humanised CDR

<400> SEQUENCE: 36

Gln Gln Trp Ser Ser His Pro Thr
1               5

<210> SEQ ID NO 37
<211> LENGTH: 12
<212> TYPE: PRT
<213> ORGANISM: Artificial Sequence
<220> FEATURE:
<223> OTHER INFORMATION: humanised CDR

<400> SEQUENCE: 37

Gly Phe Ser Leu Ser Thr Ser Gly Leu Gly Val Thr
1               5                   10

<210> SEQ ID NO 38
<211> LENGTH: 16
<212> TYPE: PRT
<213> ORGANISM: Artificial Sequence
<220> FEATURE:
<223> OTHER INFORMATION: humanised CDR

<400> SEQUENCE: 38

Leu Ile Tyr Trp Asp Asp Asp Lys Arg Tyr His Pro Ser Leu Lys Ser
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: humanised CDR

<400> SEQUENCE: 39

Ala Arg Arg Ala Leu Gly Thr Phe Asp Tyr
1               5                   10

<210> SEQ ID NO 40
<211> LENGTH: 11
```

```
<212> TYPE: PRT
<213> ORGANISM: Artificial Sequence
<220> FEATURE:
<223> OTHER INFORMATION: humanised CDR

<400> SEQUENCE: 40

Arg Ala Ser Gln Asp Ile Ser His Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: humanised CDR

<400> SEQUENCE: 41

Tyr Thr Ser Arg Leu His Ser
1               5

<210> SEQ ID NO 42
<211> LENGTH: 9
<212> TYPE: PRT
<213> ORGANISM: Artificial Sequence
<220> FEATURE:
<223> OTHER INFORMATION: humanised CDR

<400> SEQUENCE: 42

Gln Gln Gly His Thr Leu Pro Pro Thr
1               5

<210> SEQ ID NO 43
<211> LENGTH: 5
<212> TYPE: PRT
<213> ORGANISM: Artificial Sequence
<220> FEATURE:
<223> OTHER INFORMATION: humanised CDR

<400> SEQUENCE: 43

Ser Tyr Ile Met His
1               5

<210> SEQ ID NO 44
<211> LENGTH: 17
<212> TYPE: PRT
<213> ORGANISM: Artificial Sequence
<220> FEATURE:
<223> OTHER INFORMATION: humanised CDR

<400> SEQUENCE: 44

Tyr Ile Asn Pro Tyr Asn Asp Asn Thr Lys Asn Asn Glu Lys Phe Lys
1               5                   10                  15

Gly

<210> SEQ ID NO 45
<211> LENGTH: 11
<212> TYPE: PRT
<213> ORGANISM: Artificial Sequence
<220> FEATURE:
<223> OTHER INFORMATION: humanised CDR

<400> SEQUENCE: 45

Met Asp Tyr Gly Asp Tyr Pro Tyr Phe Asp Tyr
1               5                   10

<210> SEQ ID NO 46
```

```
<211> LENGTH: 11
<212> TYPE: PRT
<213> ORGANISM: Artificial Sequence
<220> FEATURE:
<223> OTHER INFORMATION: humanised CDR

<400> SEQUENCE: 46

Arg Ala Ser Gln Asp Ile Ser Asn Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: humanised CDR

<400> SEQUENCE: 47

Tyr Thr Ser Arg Leu His Ser
1               5

<210> SEQ ID NO 48
<211> LENGTH: 9
<212> TYPE: PRT
<213> ORGANISM: Artificial Sequence
<220> FEATURE:
<223> OTHER INFORMATION: humanised CDR

<400> SEQUENCE: 48

Gln Gln Gly Asn Thr Leu Pro Phe Thr
1               5

<210> SEQ ID NO 49
<211> LENGTH: 5
<212> TYPE: PRT
<213> ORGANISM: Artificial Sequence
<220> FEATURE:
<223> OTHER INFORMATION: humanised CDR

<400> SEQUENCE: 49

Asp His Tyr Met Tyr
1               5

<210> SEQ ID NO 50
<211> LENGTH: 17
<212> TYPE: PRT
<213> ORGANISM: Artificial Sequence
<220> FEATURE:
<223> OTHER INFORMATION: humanised CDR

<400> SEQUENCE: 50

Thr Ile Ser Asp Gly Gly Arg His Thr Tyr Tyr Pro Asp Ser Val Lys
1               5                   10                  15

Gly

<210> SEQ ID NO 51
<211> LENGTH: 8
<212> TYPE: PRT
<213> ORGANISM: Artificial Sequence
<220> FEATURE:
<223> OTHER INFORMATION: humanised CDR

<400> SEQUENCE: 51

Asp Leu Gly Lys Ala Leu Asp Tyr
1               5
```

```
<210> SEQ ID NO 52
<211> LENGTH: 11
<212> TYPE: PRT
<213> ORGANISM: Artificial Sequence
<220> FEATURE:
<223> OTHER INFORMATION: humanised CDR

<400> SEQUENCE: 52

Arg Ala Ser Glu Asn Ile Tyr Ser Asn Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: humanised CDR

<400> SEQUENCE: 53

Ala Ala Thr Asn Leu Ala Asp
1               5

<210> SEQ ID NO 54
<211> LENGTH: 9
<212> TYPE: PRT
<213> ORGANISM: Artificial Sequence
<220> FEATURE:
<223> OTHER INFORMATION: humanised CDR

<400> SEQUENCE: 54

Gln His Phe Trp Gly Thr Pro Trp Thr
1               5

<210> SEQ ID NO 55
<211> LENGTH: 5
<212> TYPE: PRT
<213> ORGANISM: Artificial Sequence
<220> FEATURE:
<223> OTHER INFORMATION: humanised CDR

<400> SEQUENCE: 55

Arg Tyr Ile Met Gln
1               5

<210> SEQ ID NO 56
<211> LENGTH: 17
<212> TYPE: PRT
<213> ORGANISM: Artificial Sequence
<220> FEATURE:
<223> OTHER INFORMATION: humanised CDR

<400> SEQUENCE: 56

Tyr Ile Asn Pro Tyr Asn Asp Gly Thr Arg Tyr Asn Glu Lys Phe Lys
1               5                   10                  15

Gly

<210> SEQ ID NO 57
<211> LENGTH: 11
<212> TYPE: PRT
<213> ORGANISM: Artificial Sequence
<220> FEATURE:
<223> OTHER INFORMATION: humanised CDR

<400> SEQUENCE: 57

Phe Gly Phe Gly Asp Tyr Leu Tyr Phe Asp Tyr
1               5                   10
```

```
<210> SEQ ID NO 58
<211> LENGTH: 11
<212> TYPE: PRT
<213> ORGANISM: Artificial Sequence
<220> FEATURE:
<223> OTHER INFORMATION: humanised CDR

<400> SEQUENCE: 58

Arg Ala Ser Gln Asp Ile Arg Asn Tyr Leu Asn
1               5                   10

<210> SEQ ID NO 59
<211> LENGTH: 7
<212> TYPE: PRT
<213> ORGANISM: Artificial Sequence
<220> FEATURE:
<223> OTHER INFORMATION: humanised CDR

<400> SEQUENCE: 59

Tyr Thr Ser Arg Leu His Ser
1               5

<210> SEQ ID NO 60
<211> LENGTH: 9
<212> TYPE: PRT
<213> ORGANISM: Artificial Sequence
<220> FEATURE:
<223> OTHER INFORMATION: humanised CDR

<400> SEQUENCE: 60

Gln Gln Gly Asn Thr Leu Pro Tyr Thr
1               5
```

IMMUNOMODULATORY ANTIBODIES

This Application is a national stage filing under 35 U.S.C. § 371 of International Application No. PCT/EP2016/076747, entitled "Immunomodulatory Antibodies," filed Nov. 4, 2016, which claims priority under 35 USC 119 (a)-(d) to patent application serial number GB 1519481.4, filed Nov. 4, 2015. The contents of these applications are incorporated herein by reference in their entireties.

INTRODUCTION

The present invention provides novel antibodies specific for OX40 and 4-1BB antigens, as well as methods for using such antibodies, uses of the antibodies and synergistic interactions between the antibodies in therapeutic applications.

Immunomodulatory monoclonal antibodies (mAb) constitute a novel class of clinical reagent designed to promote either endogenous or vaccine mediated anti-cancer T-cell immunity. A number of immunomodulatory mAb are now being tested in clinical trials. Encouraging data with objective responses and survival benefits have been seen with ipilumumab in metastatic melanoma (Hodi et al, *Improved survival with ipilimumab in patients with metastatic melanoma. N Engl J Med.* 363 (2010):711-23). This so-called checkpoint blocker has now been now approved for this melanoma and anti-PD-1/PD-1L is also delivering positive outcomes in various cancers including lung and melanoma (J. R. Brahmer et al, *Safety and activity of anti-PD-L1 antibody in patients with advanced cancer. N Engl J Med,* 366 (2012), p. 2455-2465). However, there have also been negative studies, and autoimmune toxicity is a recognised hazard, with manifestations such as colitis, thyroiditis and hypophysitis well documented.

The present invention is a result of study focused on two receptors belonging to the tumour necrosis factor receptor superfamily (TNFRSF): 4-1BB and OX40. Anti-4-1BB and anti-OX40 mAbs have both shown excellent efficacy in preclinical investigations, including combined synergistic potency (Gray et al, *Eur J Immunol,* 2008 38(9):2499-511). *Optimising anti-tumour CD8 T-cell responses using combinations of immunomodulatory antibodies.* 2008) and both are in early clinical trials where they have been reasonably well tolerated and indicate modest therapeutic potential (Curti et al, *Cancer Res.* 2013 Dec. 15; 73(24):7189-98. 74. *OX40 is a potent immune-stimulating target in late-stage cancer patients.* ↵ Sznol M, et al. *J Clin Oncol* 26: 2008 (May 20 suppl; abstr 3007). *Phase I study of BMS-663513, a fully human anti-CD137 agonist monoclonal antibody, in patients (pts) with advanced cancer;* Segal et al, 2014 ASCO Annual Meeting Abstract Number: 3007 Citation: *J Clin Oncol* 32:5s, 2014 (suppl; abstr 3007). *A phase 1 study of PF-05082566 (anti-4-1BB) in patients with advanced cancer.*)

Data from the laboratory of the inventors has demonstrated the critical role for isotype in the immunostimulatory activity of anti-mouse CD40 mAbs showing that the mouse IgG1 isotype stimulates both the humoral and cell-mediated arms of the immune system, whereas anti-CD40 IgG2a does not and that this is dependent on the inhibitory FcγRIIb (White et al, *J Immunol.* 2011 Aug. 15; 187(4):1754-63. *Interaction with FcγRIIB is critical for the agonistic activity of anti-CD40 monoclonal antibody;* also Li et al, *Science.* 2011 Aug. 19; 333(6045):1030-4. *Inhibitory Fcγ receptor engagement drives adjuvant and anti-tumor activities of agonistic CD40 antibodies*). Furthermore, they have shown that when considering human IgG, IgG2 is more active than IgG1, and that this activity is independent of the requirement for FcγRs (White et al, *Cancer Cell.* 2015 Jan. 12; 27(1): 138-48. *Conformation of the human immunoglobulin G2 hinge imparts superagonistic properties to immunostimulatory anticancer antibodies*). These are key observations with important implications for the development of the new immunostimulatory mAb, and in the light of these some of the mAbs used in the clinic to date (anti-4-1BB, BMS-663513 human IgG4, anti-OX40, 9B12, mouse IgG1) may not be optimal and so may underestimate potential clinical activity of this class of reagent.

Here we provide new mAb that have been selected for therapeutic application based on their activity in in vitro and in vivo assays to deliver reagents that are potent, yet with manageable side effects for the treatment of cancer.

SUMMARY OF THE INVENTION

In a first aspect, there is provided a monoclonal antibody or antigen binding portion thereof which specifically binds to the cysteine rich repeat sequences in extracellular domains 3 or 4 of OX40, which is preferably an antibody or antigen binding portion thereof wherein CDR3 of the variable domain of the heavy chain has a sequence identity of at least 90%, 91%, 92%, 93%, 94%, 95%, 96%, 97%, 98%, 99%, 99% or 100% with one of SEQ ID NO. 21, SEQ ID NO. 27, SEQ ID NO.33, SEQ ID NO. 39, SEQ ID NO. 45, SEQ ID NO. 51 or SEQ ID NO. 57.

In one embodiment, CDR3 of the variable domain of the heavy chain has a sequence identity of at least 95%, 96%, 97%, 98%, 99%, 99.5%, or 100% with SEQ ID NO. 57.

In embodiments, the antibodies further comprise one or more CDRs selected from any one of SEQ IDs 19-20, 22-26, 28-32, 34-38, 40-44, 46-50, 52-56 or 58-60.

In one embodiment, the antibody according to this aspect of the invention can comprise heavy chain CDRs having SEQ ID Nos 19-21 and light chain CDRs having SEQ ID Nos 22-24.

In one embodiment, the antibody according to this aspect of the invention can comprise heavy chain CDRs having SEQ ID Nos 25-27 and light chain CDRs having SEQ ID Nos 28-30.

In one embodiment, the antibody according to this aspect of the invention can comprise heavy chain CDRs having SEQ ID Nos 31-33 and light chain CDRs having SEQ ID Nos 34-36.

In one embodiment, the antibody according to this aspect of the invention can comprise heavy chain CDRs having SEQ ID Nos 37-39 and light chain CDRs having SEQ ID Nos 40-42.

In one embodiment, the antibody according to this aspect of the invention can comprise heavy chain CDRs having SEQ ID Nos 43-45 and light chain CDRs having SEQ ID Nos 46-48.

In one embodiment, the antibody according to this aspect of the invention can comprise heavy chain CDRs having SEQ ID Nos 49-51 and light chain CDRs having SEQ ID Nos 52-54.

In one embodiment, the antibody according to this aspect of the invention can comprise heavy chain CDRs having SEQ ID Nos 55-57 and light chain CDRs having SEQ ID Nos 58-60.

In embodiments, the antibody is of murine isotype IgG1 or human isotype IgG2.

In a second aspect, the invention provides a monoclonal antibody (MAb) or antigen binding portion thereof which specifically binds to the cysteine rich repeat sequences in extracellular domain 1 of 4-1BB, which is preferably a monoclonal antibody or antigen binding portion thereof wherein CDR3 of the variable domain of the heavy chain has a sequence identity of at least 70%, 80%, 85%, 90%, 91%, 92%, 93%, 94%, 95%, 96%, 97%, 98%, 99%, 99% or 100% with one of SEQ ID NO. 3, SEQ ID NO. 9, or SEQ ID NO. 15 In one embodiment, CDR3 of the variable domain heavy chain has the sequence set forth in SEQ ID No. 3.

In one embodiment, CDR3 of the variable domain heavy chain has the sequence set forth in SEQ ID No. 9.

In one embodiment, the CDR3 of the variable domain of the heavy chain has a sequence identity of at least 95%, 96%, 97%, 98%, 99%, 99.5%, or 100% with SEQ ID NO. 15.

In one embodiment, CDR3 of the variable domain heavy chain has the sequence set forth in SEQ ID No. 15.

In embodiments, the antibodies further comprise one or more CDRs selected from any one of SEQ IDs 1-2, 4-8, 10-14 or 16-18.

In one embodiment, the antibody according to this aspect of the invention can comprise heavy chain CDRs having SEQ ID Nos 1-3 and light chain CDRs having SEQ ID Nos 4-6.

In one embodiment, the antibody according to this aspect of the invention can comprise heavy chain CDRs having SEQ ID Nos 7-9 and light chain CDRs having SEQ ID Nos 10-12.

In one embodiment, the antibody according to this aspect of the invention can comprise heavy chain CDRs having SEQ ID Nos 13-15 and light chain CDRs having SEQ ID Nos 16-18.

In embodiments, the antibody is of murine isotype IgG1 or human isotype IgG2.

In the above aspects of the invention, the antibody can be selected from a human antibody, a chimeric antibody containing a human variable region, a humanized antibody, a bispecific antibody, or a single chain antibody, as well as antigen-binding fragments thereof.

OX40 antagonists are useful in the treatment of autoimmune and inflammatory conditions, where an excessive immune response needs to be regulated. According to a third aspect, there is provided an antibody as set forth in the second aspect of the invention, for use in inhibiting OX40 signalling. For example, therefore, the disease treated by the present invention is an autoimmune or inflammatory condition, and the anti-OX40 antibody is an OX40 or OX40L antagonist. Preferably, the OX40 antagonist has a CDRH3 sequence at identity of at least 95%, 96%, 97%, 98%, 99%, 99.5%, or 100% with SEQ ID No. 51.

For example, an antagonistic antibody is useful in the treatment of autoimmune disease or inflammation.

In a fourth aspect of the invention, there are provided anti-4-1BB and/or anti-OX40 antibodies according to the previous aspects of the invention for use in the treatment of disease. In one embodiment, anti-4-1BB antibodies and anti-OX40 antibodies may be coadministered. The coadministration may be combined or sequential. In another embodiment, anti-4-1BB antibodies are administered, without anti-OX40 antibodies. In another embodiment, anti-OX40 antibodies are administered, without anti-4-1BB antibodies.

According to a further aspect, the invention provides a method for stimulating anti-tumour T cell immunity comprising administering to a subject in need thereof a therapeutically effective amount of a stimulatory antibody according to the previous aspects of the invention or a combination of at least one anti-4-1BB and at least one anti-OX40 antibody according to said foregoing aspects.

The foregoing embodiments may be combined to form a combined preparation for administration, or may be administered separately; we have noted that administration of the antibodies such that they are present at the same time, whether by simultaneous, simultaneous separate or sequential administration, results in therapeutic effects.

Sequential administration of the antibodies can be performed in any desired order. For example the anti-4-1BB antibody can be administered before the anti-OX40 antibody, or the anti-OX40 antibody can be administered before the anti-4-1BB antibody.

The variable domains of the aforementioned antibodies may be lambda or kappa light chains. Preferably, the light chains are kappa light chains. Light chains may be from any kappa or lambda family. Preferred families include Vk6 and Vk2. Heavy chains may be from any heavy chain variable region family; preferred are Vh2, Vh4, Vh6 and Vh7.

The constant region of any one or more antibodies is preferably mouse IgG1 or human IgG2. In human or humanised antibodies, at least the presence of an IgG2 hinge region is preferred.

Antibodies may be agonistic or inhibitory. Agonistic and inhibitory antibodies can be put to different uses for the treatment of disease. For the treatment of cancer, agonistic antibodies are indicated. In embodiments, therefore, the antibodies in the foregoing aspects of the invention are agonistic. For example, stimulation of anti-tumour T cell immunity increases CD4+ and/or CD8+ T cell accumulation in the cancer cell-containing sites of a tumour. We have shown that antibodies using mIgG1 constant regions are more effective agonists, even when the parent antibody is isolated as a member of another IgG isotype.

The number of times the antibody has given >50% stimulation over control/Total number of experiments in which the antibody was included.

The shading represents the hOX40 domain(s) recognised by the antibodies (see C)

B: Example of proliferation results obtained with PBMCs from one donor.

C: WT and Δ1 and Δ1Δ2 forms of hOX40 were constructed and expressed transiently in 293F cells and the anti-OX40 antibodies tested for binding to the three forms of h4-1BB. The histogram shows the binding pattern of SAP25.29.

Figure 2:
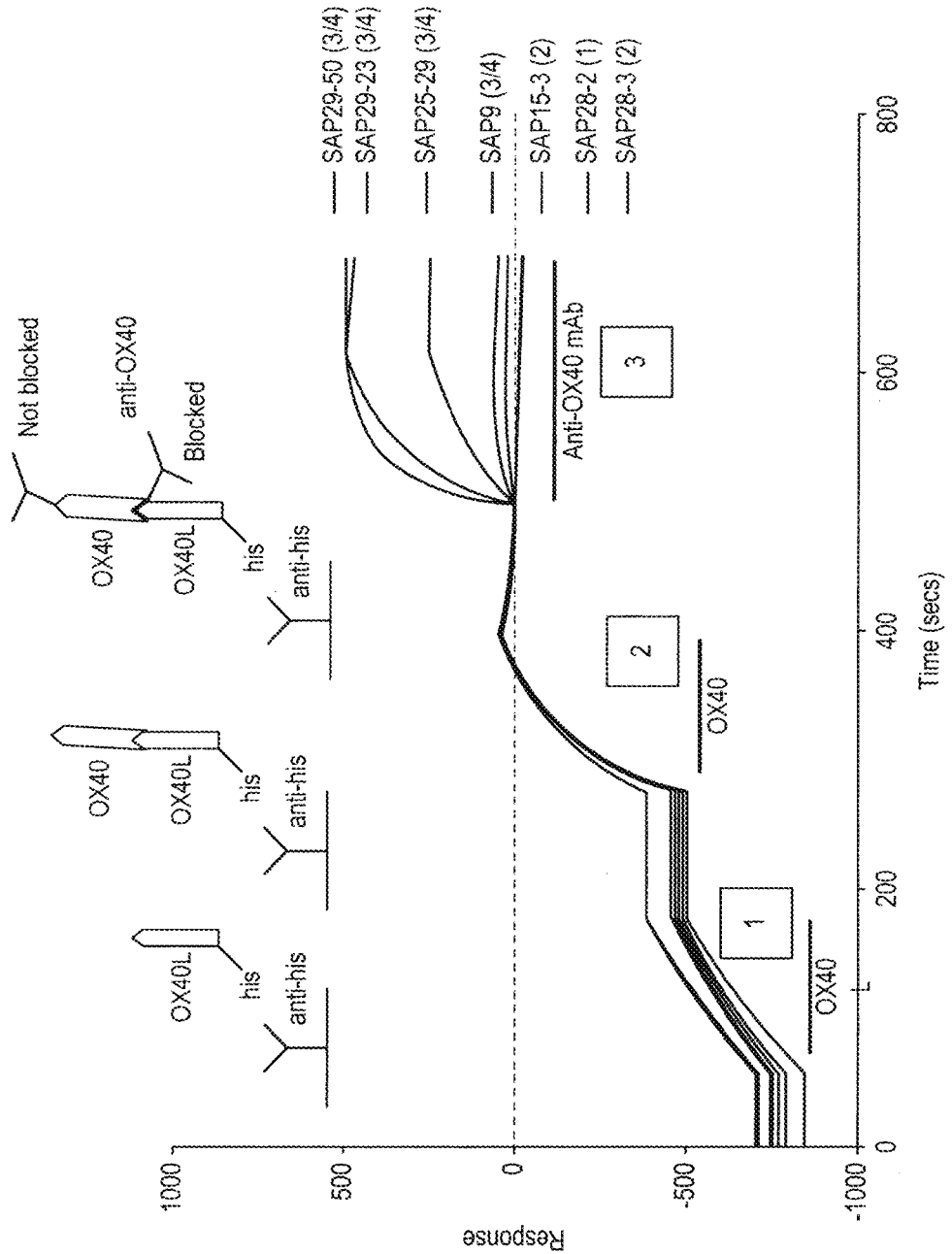

FIG. 2 The effect of the interaction between OX40L and OX40 on the binding of anti-OX40 mAbs determined using Biacore analysis His-tagged OX40L (1) and OX40 (2) were sequentially passed over an anti-his Biacore chip to visualise the OX40L/OX40 interaction. Anti-OX40 mAbs were then passed over (3) to determine whether their binding was blocked when OX40 was bound to OX40L. SAP28-2 which binds to domain 1 of OX40, and SAP15-3 and SAP28-3 which bind domain 2 were blocked by the interaction of OX40 with OX40L. SAP9 which binds in domains 3/4 was also blocked, but three other mAbs which also bind domains 3/4, SAP25-29, SAP29-50 and SAP29-23 were not blocked.

Figure 3:
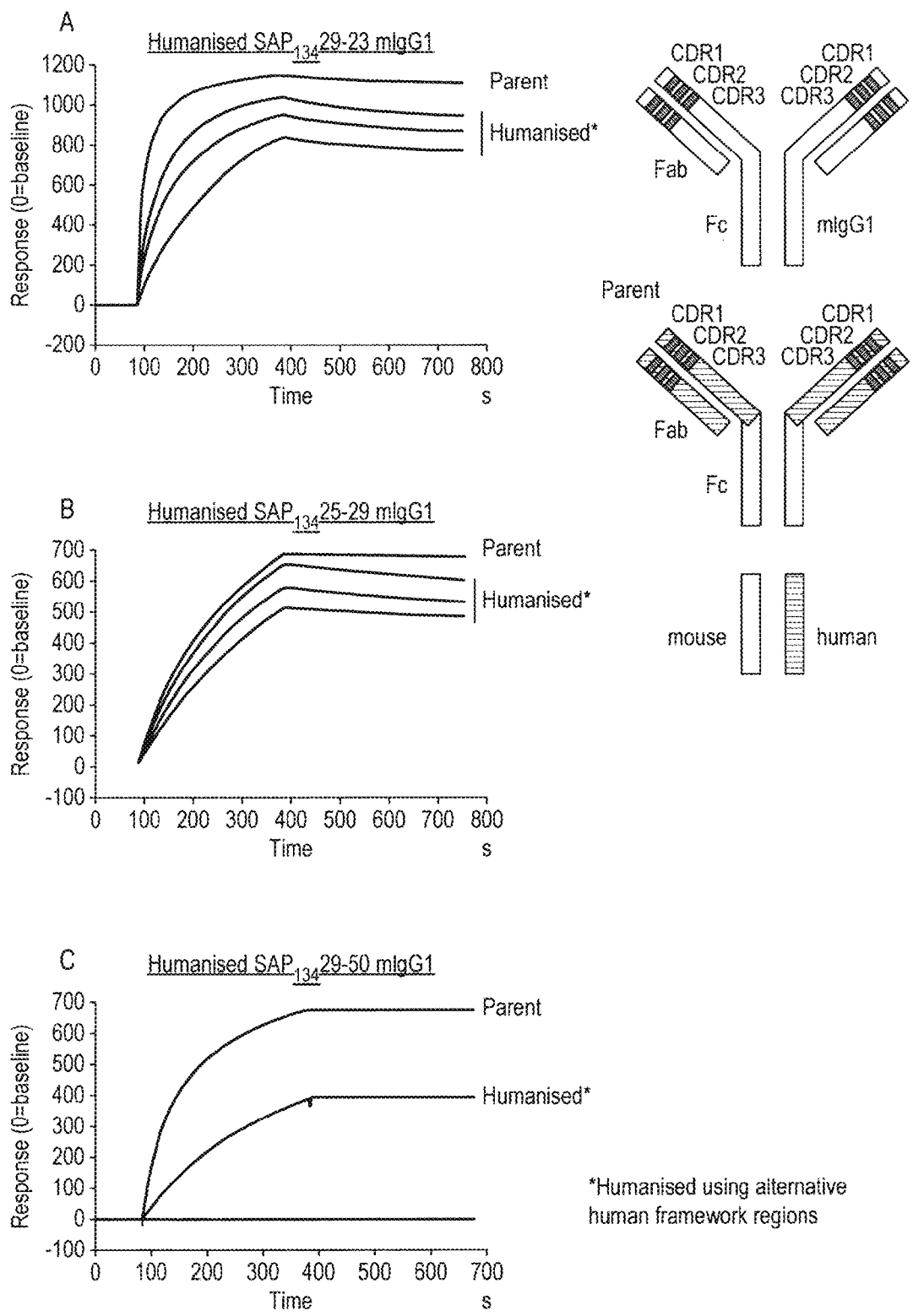

FIG. 3 Comparison of the binding of parental and humanised anti-hOX40 antibodies using Biacore analysis.

The CDRs of the parental antibody were identified and grafted into appropriate human variable framework (FR) regions, linked to mIgG1 constant regions. In some cases, the mouse FR3 was retained. The cartoons show the structure of the humanised antibodies: note that humanised Fab regions with the 3 mouse CDRS are combined with the mouse IgG1 Fc region.

A and B: SAP29-23 and SAP25-29 with three different human Fab framework regions (FR) retained their binding activity. However, the dissociation rate of the humanised antibodies appeared faster than that of the parent antibodies.

C: SAP29-50 also retained binding activity after humanisation, and the dissociation rate appeared comparable with that of the parent mAb. However, the humanised antibody was produced with very low yield.

Figure 4:
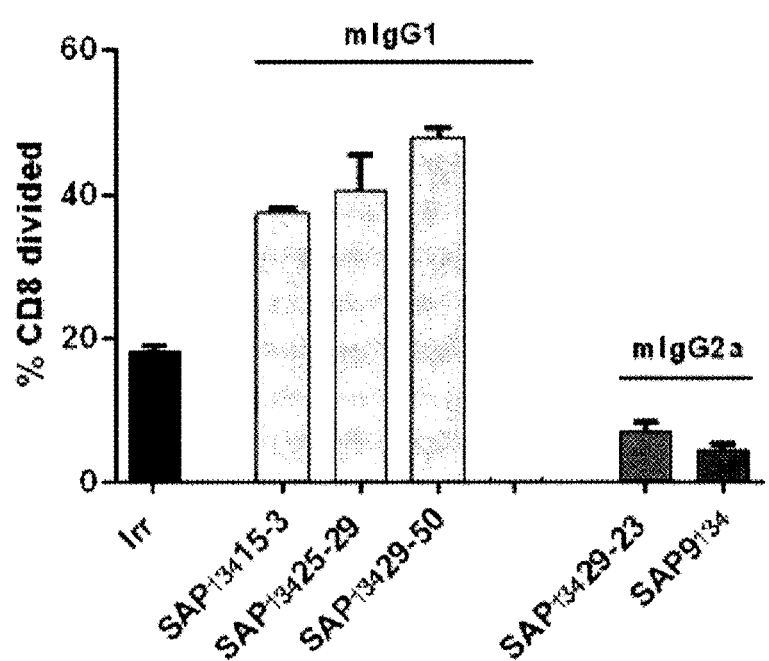

FIG. 4 Anti-OX40 antibodies with the mIgG1 isotype stimulate T-cell proliferation whereas those with the IgG2a isotype are inactive or even inhibitory.

Figure 1:
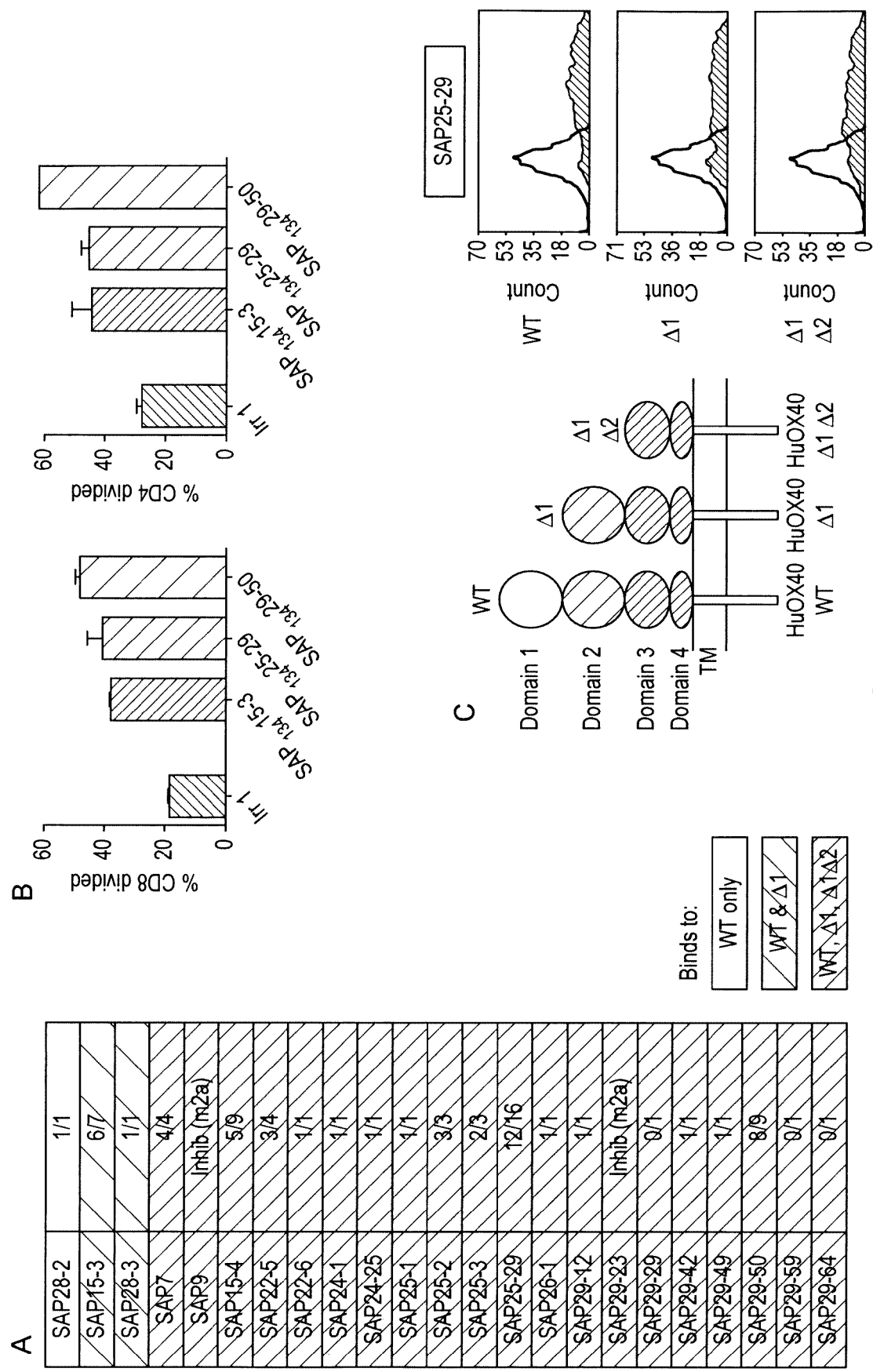
FIG. 1 In vitro stimulation of peripheral blood T-cell proliferation by anti-OX40 antibodies and identification of the extracellular domains recognised A and B: T-cell proliferation was assessed using a CFSE dilution technique: healthy donor PBMCs were labelled with 2 μM CFSE and stimulation of CD8 and CD4 proliferation in the presence of a sub-optimal concentration of plate-bound OKT3 and 5 μg/ml soluble anti-OX40 antibody determined by after 5-7 days by flow cytometry.

Assays were as described in FIG. 1.

Figure 5:
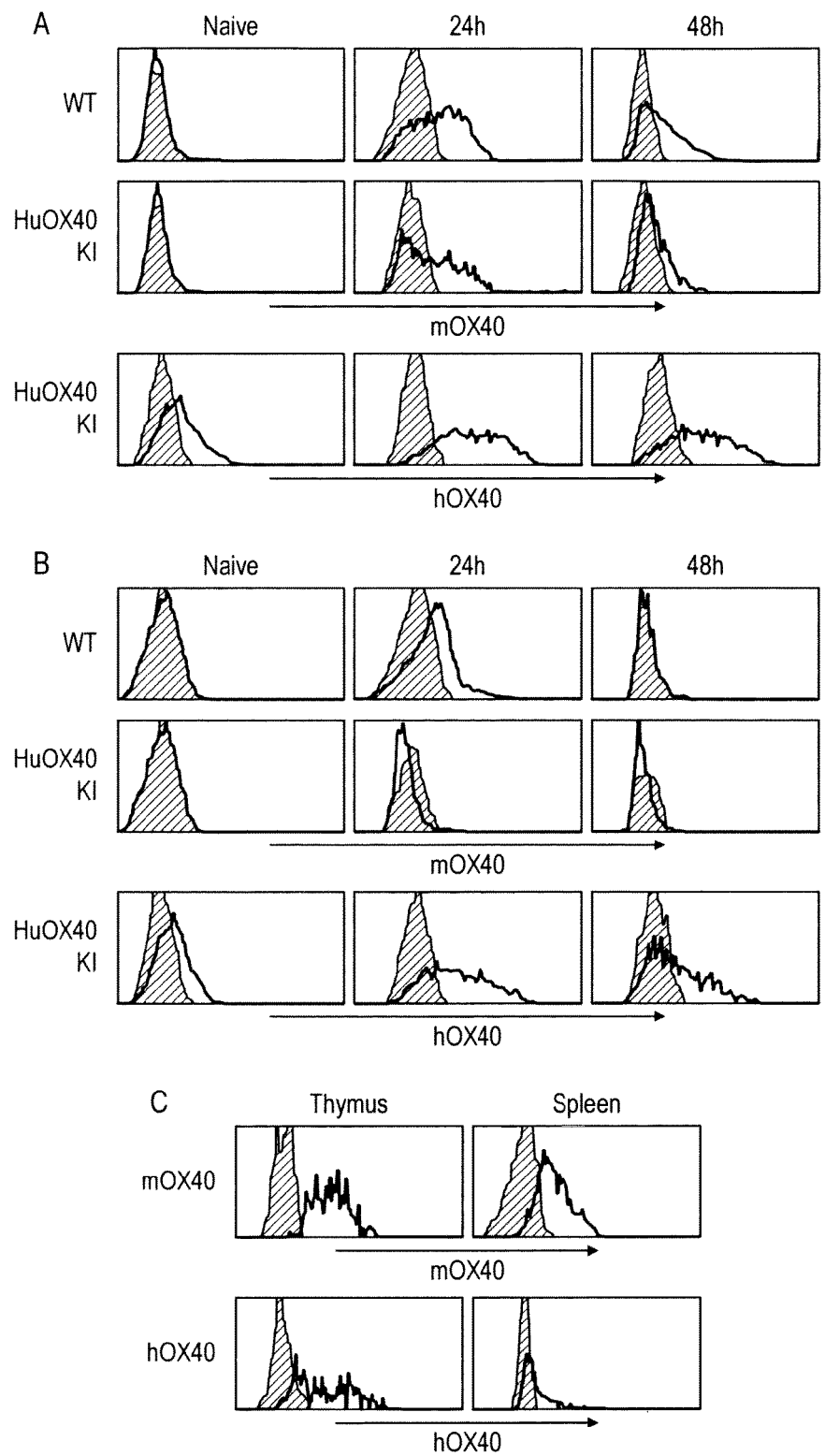

FIG. 5 Comparison of mOX40 and hOX40 expression on CD4 and CD8 T cells in heterozygous (+/−) hOX40 knock-in (KI) mice.

Expression of mOX40 and hOX40 on CD4 (A) and CD8 (B) T cells following activation of splenocytes in WT and hOX40 KI mice. C, Expression of mOX40 and hOX40 on thymic and splenic Treg in hOX40 KI mice.

Figure 6:
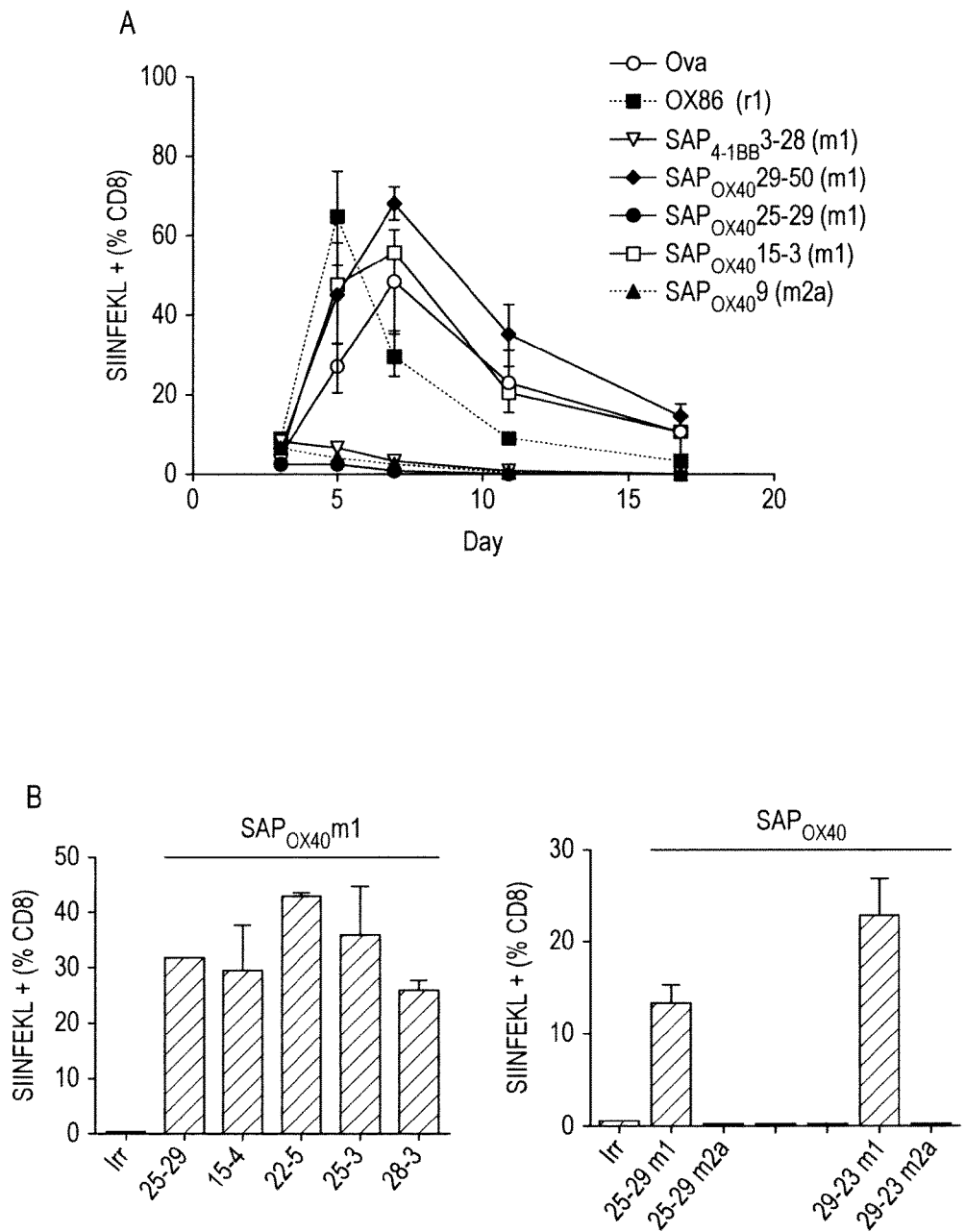
Figure 6:
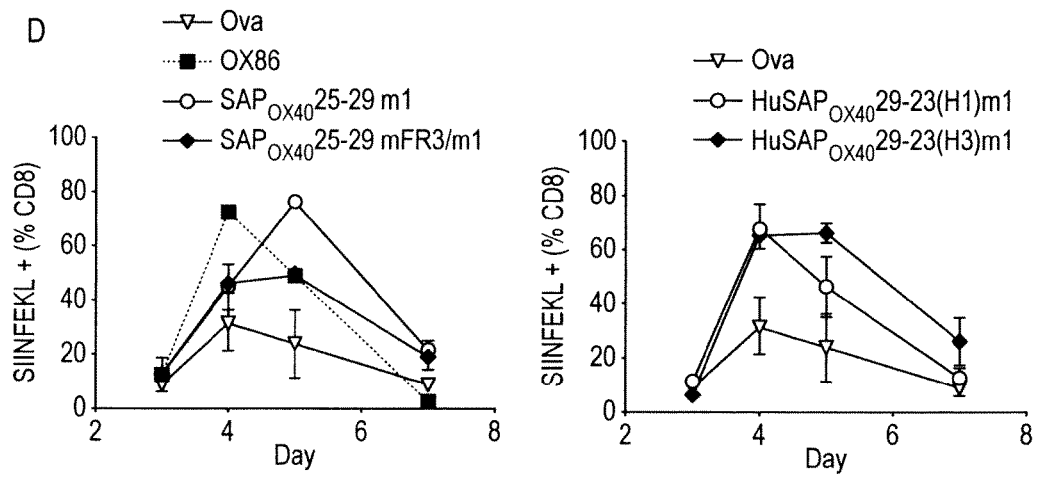

FIG. 6 Comparison of the effect of anti-mOX40 and anti-hOX40 mAb on the expansion of OT1 cells in vivo Splenocytes from OT-I x heterozygous hOX40 (+/−) mice were transferred i.v. into WT recipients. 24 h later recipients received Ova (0.5 mg) and either control, anti-mOX40 (OX86), or mIgG1 or mIgG2a anti-hOX40 mAb. The level of OT-I SIINFEKL+ cells in the blood was monitored by flow cytometry. A. Time course of responses to representative antibodies. B. Comparison of response at day 6 from a range of m1 and m2a antibodies. C. Table showing relative responses with all antibodies tested so far. D. Time courses of responses to humanised anti-hOX40 antibodies (linked to mIgG1 constant regions).

Figure 7:
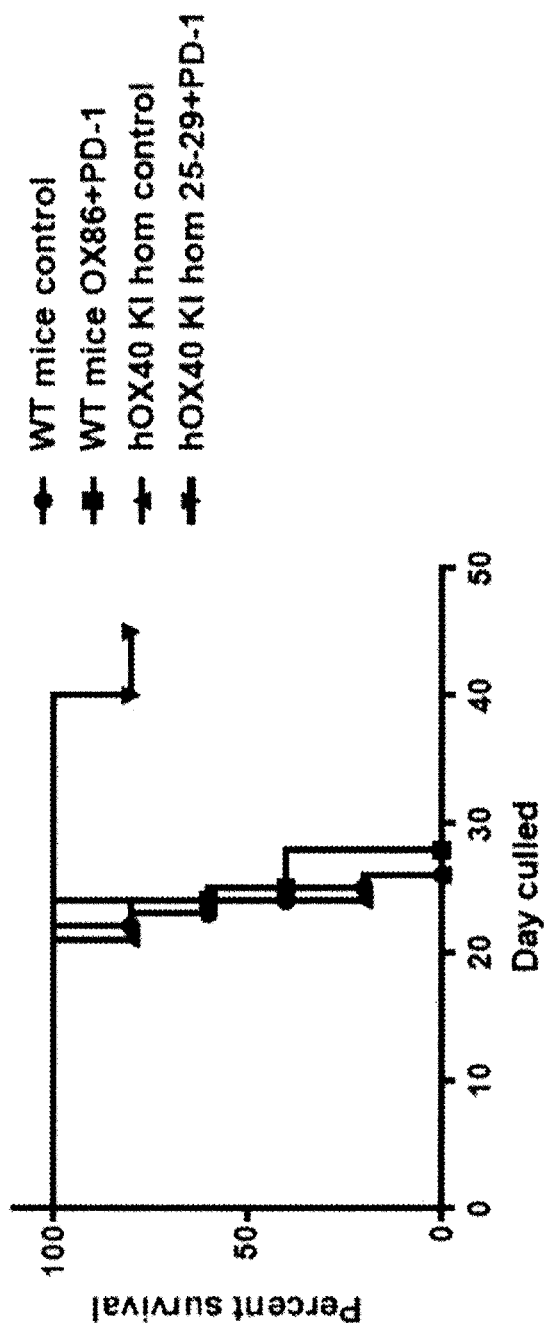

FIG. 7 SAP25-29 was is efficacious in combination with an anti-PD1 antibody in the C1498 mouse model of acute myeloid leukaemia Homozygous hOX40 KI or WT mice were given 1×10⁶ C1498 cell i.v., the 150 mg of anti-PD-1, SAP25-29, or a combination given on days 7, 10, 12, 14, and 17. Survival was monitored.

Figure 8:
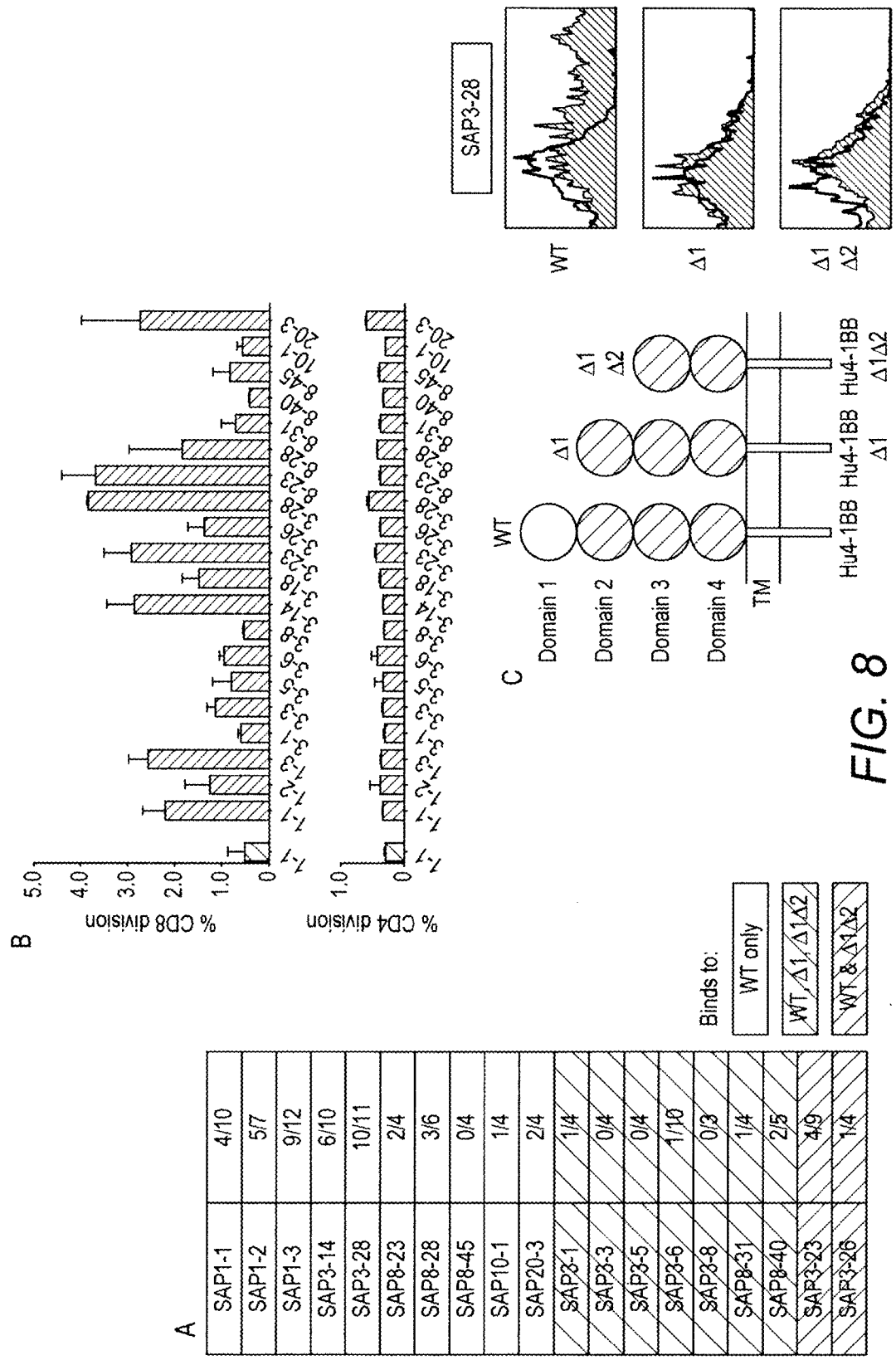

FIG. 8 In vitro stimulation of peripheral blood T-cell proliferation by anti-4-1BB antibodies and identification of the extracellular domains recognised A and B: T-cell proliferation was assessed using a CFSE dilution technique: healthy donor PBMCs were labelled with 2 μM CFSE and stimulation of CD8 and CD4 proliferation in the presence of a sub-optimal concentration of plate-bound OKT3 and 5 μg/ml soluble anti-4-1BB antibody determined by after 5-7 days by flow cytometry.

A: The figures in the right hand represent:

The number of times the antibody has given >50% stimulation over control/Total number of experiments in which the antibody was included.

The shading represents the 4-1BB domain(s) recognised by the antibodies (see C)

B: show an example of the results obtained with one donor.

C: WT and Δ1 and Δ1Δ2 forms of h4-1BB were constructed and expressed transiently in 293F cells and the anti-4-1BB antibodies tested for binding to the three forms of h4-1BB. The histogram shows the binding pattern of SAP3-28.

Figure 9:
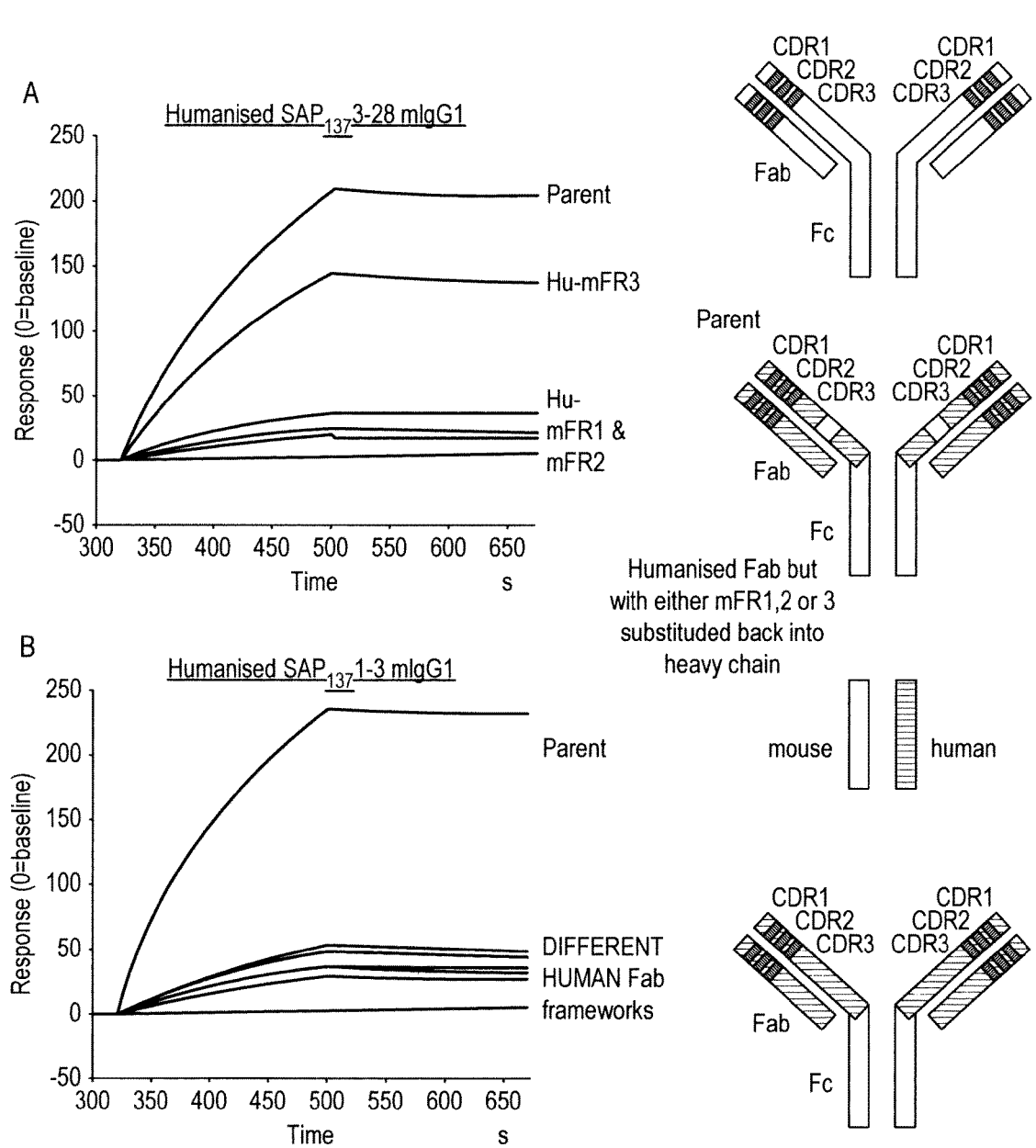

FIG. 9 Comparison of the binding of parental and humanised anti-h4-1BB antibodies using Biacore analysis.

The CDRs of the parental antibody were identified and grafted into appropriate human variable framework (FR) regions, linked to mIgG1 constant regions. In some cases, the mouse FR3 was retained. The cartoons show the structure of the humanised antibodies.

A: SAP3-28 with fully human Fab framework regions (FR) showed no binding activity (results not shown). However, when mouse FR3 was substituted for human FR3, binding activity was restored.

B: SAP1-3 lost binding activity on humanisation.

Figure 10:
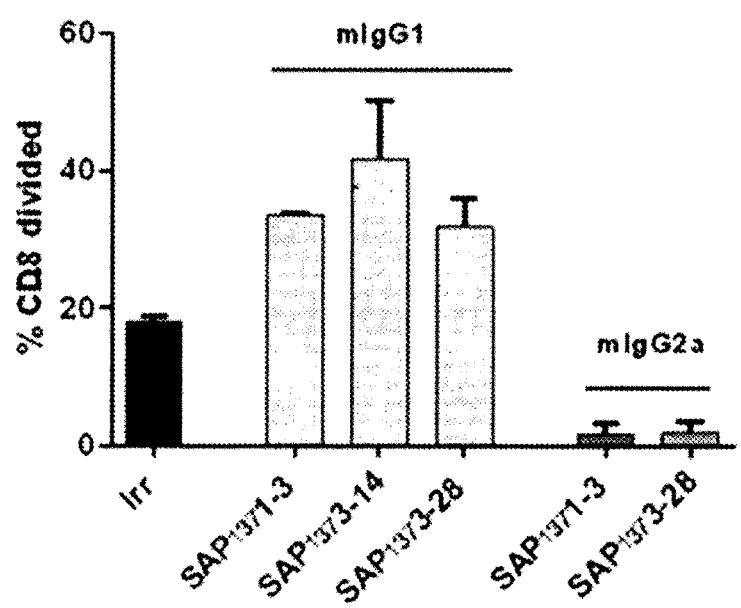

FIG. 10 Anti-4-1BB antibodies with the mIgG1 isotype stimulate T-cell proliferation whereas those with the IgG2a isotype are inactive or even inhibitory.

Assays were as described in FIG. 1.

Figure 11:
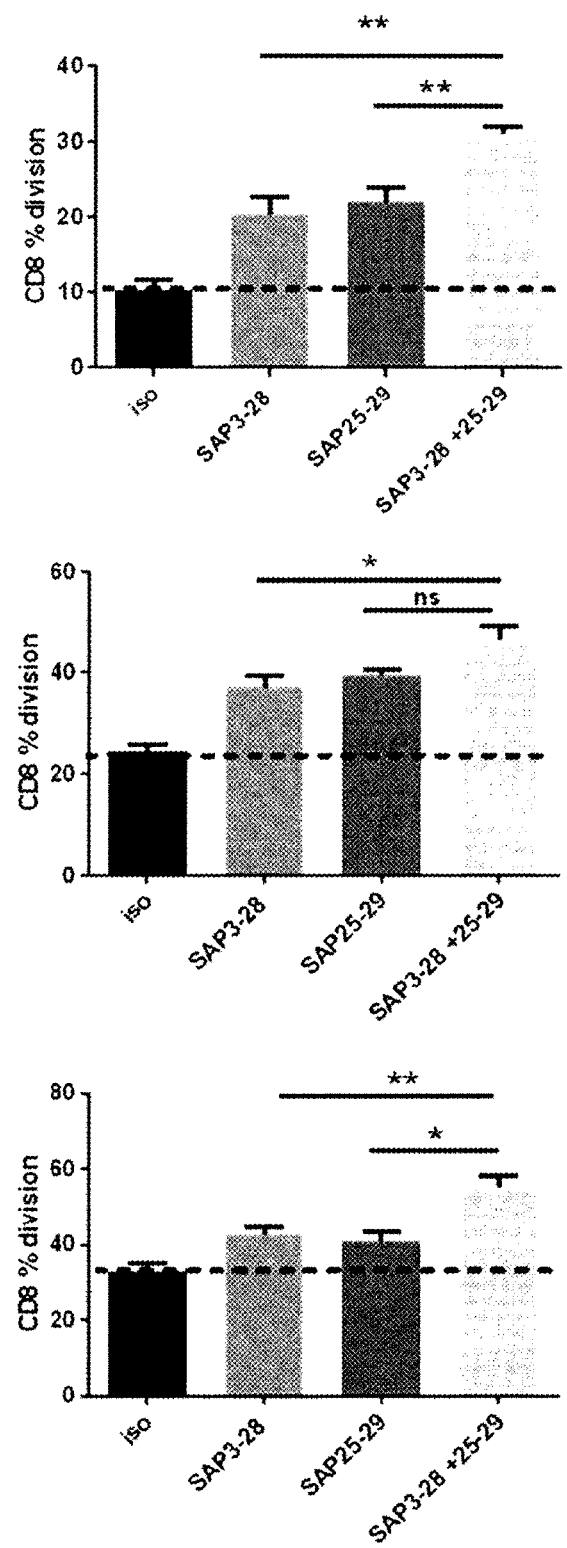

FIG. 11 A combination of anti-h4-1BB and anti-hOX40 mAbs results in greater costimulation of CD8 T cells than the single mAbs T-cell proliferation was determined as described in FIG. 1 (5 μg/ml single mAbs, 5 μg/ml of each for the combination). Results with PBMCs isolated from 3 donors are shown. * $p<0.05$, ** $p<0.01$.

DETAILED DESCRIPTION OF THE INVENTION

Unless defined otherwise, all technical and scientific terms used herein have the same meaning as commonly understood by those of ordinary skill in the art, such as in the arts of peptide chemistry, cell culture and phage display, nucleic acid chemistry and biochemistry. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Standard techniques are used for molecular biology, genetic and biochemical methods ("Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction" (Mullis, 1994); "Current Protocols in Immunology" (Coligan, 1991)), which are incorporated herein by reference. These techniques are applicable to the production of the polynucleotides and polypeptides of the invention, and, as such, may be considered in making and practicing the invention. Particularly useful techniques for particular embodiments will be discussed in the sections that follow.

An "antibody" may be selected from, but not limited to, an IgG, IgA, or an antigen binding antibody fragment selected from an antibody single variable domain polypeptide, dAb, FAb, F(ab')2, an scFv, an Fv, a $V_{HH}$ domain (such as a Nanobody® or other camelized immunoglobulin domain) or a disulfide-bonded Fv. In certain embodiments, any of the above antibody types or fragments thereof may be prepared from one or more of a mammalian species selected from, but not limited to mouse, rat, rabbit, human. Such antibodies can be humanized for use in humans.

In certain embodiments, any of the above antibody types or fragments thereof may be provided as heteroconjugates, bispecific, single-chain, chimeric or humanized molecules having affinity for OX40 and/or 4-1BB as appropriate.

In certain embodiments, any of the aforementioned antibody/antibodies binds to OX40 and/or 4-1BB with a dissociation coefficient of 100 nM or less, 75 nM or less, 50 nM or less, 25 nM or less, such as 10 nM or less, 5 nM or less, 1 nM or less, or in embodiments 500 pM or less, 100 pM or less, 50 pM or less or 25 pM or less.

Antibodies may be monospecific, with narrow or broad specificity; or multispecific, such as bispecific, such that they possess two distinct epitope specificities in a single antibody molecule. Cocktails of antibodies may be targeted at two or more specific epitopes. Antibody cocktails may be prepared by admixture of one or more monoclonal antibodies. In one embodiment, an antibody cocktail contains two, three, four or more monoclonal antibodies each of which agonises or antiagonises OX40 and/or 4-1BB, as set out herein.

In one embodiment, the antibody is monoclonal and binds a unique structural motif on OX40 or 4-1BB or a bi- or multivalent antibody that binds to any combination of OX40 and 4-1BB.

In one aspect, the antibody or antibodies of the invention are formulated for intravenous (iv) or intramuscular (im) administration. Antibodies administered iv should extravasate from the circulation in order to enter the interstitial tissue space and bind to their cognate target.

The antibody, in one embodiment, is an antibody fragment such as a scFv, dAb or $V_{HH}$ antibody. Small antibody fragments are extravasated much more readily into tissue, and for this reason can perform better than IgG or other larger antibodies. However, smaller fragments are also cleared faster from the circulation. A compromise must be struck between tissue accessibility and clearance. For example, see Wang et al., Clinical pharmacology & Therapeutics, 84:5, 2008, 548-558. Several antibody conjugates have been described which have extended half-life using a variety of strategies, for example through conjugation to albumin (such as human serum albumin). See Kontermann et al., BioDrugs April 2009, Volume 23, Issue 2, pp 93-109.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Members of the TNFRSF are Key Targets for Immunomodulatory mAb

Members of the TNFRSF constitute 3% of all leukocyte cell surface proteins. They are type I transmembrane proteins that adopt elongated structures due to the presence of multiple ~40 amino acid cysteine-rich repeats (CRR) within their extracellular regions. The receptors, which share only ~25% identity within their extracellular regions, interact with diverse proteins that belong to the TNF and immunoglobulin superfamilies (Croft, 2003; Locksley et al., 2001; Watts, 2005). They play essential roles in regulating the adaptive immune response and are particularly important for sustaining T-cell survival. Structural studies have demonstrated that the homotrimeric ligands associate with three monomeric receptors (Jones, 2000; Locksley et al., 2001). Based on these studies ligand-mediated receptor trimerisation was proposed as a mechanism of transmembrane signalling. Subsequent studies, however, have suggested that ligand binding triggers conformational changes within already associated receptors (Locksley et al., 2001). Our own studies examining the oligomeric requirements for signalling by the TNFRSF members CD30, CD40, and 4-1BB have shown that trimeric ligands do not trigger optimal responses and that higher order oligomers, possibly two adjacent trimers, generate transmembrane signals more effectively (Hargreaves and Al-Shamkhani, 2002; Haswell et al., 2001; Rowley and Al-Shamkhani, unpublished observations). The finding that soluble shed trimeric Fas ligand is less potent than its membrane-anchored form supports this idea (Suda et al., 1997). Although the use of soluble oligomeric ligands in vivo is hampered by their lack of stability and short half-life, assessment of the oligomeric requirements for signalling by TNFRSF members has direct implications for developing agonistic mAb.

The TNFRSF can be divided into two sub-families based on the presence or absence of a death domain (DD), a protein module that allows coupling to caspase 8/10 and the induction of apoptosis. Members of the TNFRSF that lack the DD are the targets of the present invention. This sub-family interacts intracellularly with TNFR-associated factors (TRAFs) leading to activation of intracellular signalling pathways that promote the activation, proliferation and survival of leukocytes (Croft, 2003; Locksley et al., 2001; Watts, 2005). Two members of this sub-family (4-1BB and OX40) show promise as targets for therapeutic agents for the following reasons:

(1) Preclinical data demonstrate the critical role of these receptors in amplifying antigen specific T-cell immunity in vivo, including anti-tumour immunity.
(2) Combination of mAb directed to these two receptors may optimise anti-tumour responses because of their differential expression and function on T-cell subsets.
(3) No systematic approach has yet been taken to design immunomodulatory mAb that target these receptors. In particular, the impact of mAb epitope on the regulatory effects of 4-1BB mediated through interaction with inhibitory receptors eg. B and T cell attenuator (BTLA) and CD160 (Cai et al., 2008; Gonzalez et al., 2005; Murphy et al., 2006; Sedy et al., 2005) have not been addressed.

4-1BB (CD137)

4-1BB is expressed on activated T cells, memory CD8 T cells, NK cells, NKT cells, monocytes, dendritic cells, follicular dendritic cells, activated mast cells, and microglia. 4-1BB signalling costimulates T cells during the primary and secondary responses by enhancing their proliferation and survival (Watts, 2005). In mouse models, 4-1BB is important in recall CD8 T-cell responses to viruses and in the survival of effector/memory CD8 T cells (Watts, 2005). 4-1BB costimulation also enhances expansion, cytokine production, and cytolytic effector functions of human T cells, with effects on both CD4 and CD8 T cells (Alderson et al., 1994; Kim et al., 1998; Watts, 2005). Administration of agonistic anti-mouse 4-1BB mAb preferentially stimulates the expansion of antigen-specific CD8 T cells, reverses CD8 T cell anergy, prevents suppression by regulatory T cells, and boosts memory CD8 T cell expansion (Robertson et al., 2008; Takahashi et al., 1999; Wilcox et al., 2004; Zhu et al., 2007). Agonistic 4-1BB mAb have been explored in a number of preclinical cancer models and shown to promote rejection of a range of poorly immunogenic tumours (Melero et al., 1997; Taraban et al., 2002; Wilcox et al., 2002).

Initial clinical investigations with a human IgG4 anti-4-1BB mAb resulted in modest responses in patients with melanoma (Sznol et al., 2008; Bristol-Myers Squibb Study of BMS-663513 in Patients with Advanced Cancer Available from: clinicaltrials.gov/ct2/show/NCT00309023.NLM identifier: NCT00309023Accessed Jul. 20, 2013). The half-life of the antibody was relatively short (8-12 hours) and although CD8 expansions were seen in peripheral blood these were not sustained despite repeated dosing at 3 week intervals. It is not clear why the IgG4 isotype was chosen for this work, given the known instability of this type of antibody in vivo (van der Neut Kolfschoten et al., 2007), and this choice may account for the short half-life and low persistence of CD8 expansion.

OX40 (CD134)

OX40 is expressed on activated CD4 and CD8 T cells, regulatory CD4 T cells, memory CD4 T cells and NKT cells. OX40 signalling is critical for the survival of antigen-primed CD4 T cells and development of CD4 T cell memory (Croft, 2003). It plays a role in enhancing survival and effector cell differentiation of CD8 T cells during priming, and is important for T cell expansion during secondary responses (Bansal-Pakala et al., 2004; Lee et al., 2006). OX40 signalling has been shown to costimulate the expansion of human antigen-specific memory CD8 T cells, although this effect was mostly mediated indirectly via costimulation of CD4 helper T cells (Serghides et al., 2005). The inventors generated the first agonistic anti-OX40 mAb (Al-Shamkhani et al., 1996) that promoted anti-tumour immunity through activation of CD8 T cells (Lee et al., 2004; Song et al., 2007). OX40 mAb can also promote anti-tumour immunity via inhibition of regulatory CD4 T cell function within the tumour itself (Piconese et al., 2008; Valzasina et al., 2005; Vu et al., 2007). Advantageously, a profound synergistic activity has been demonstrated between anti-OX40 with anti-4-1BB mAb on anti-tumour T-cell immunity (Gray et al, E J Immunol, 2008), which may have important implications for future immunotherapy.

Co-Administration

We have described beneficial coadministration of antibodies which act as agonists for OX40 and 4-1BB. In particular, we show a beneficial effect for antibodies which are directed to the cysteine rich repeat sequences in extracellular domain 1 of 4-1BB and to the cysteine rich repeat sequences in extracellular domains 3 or 4 of OX40. In embodiments, the 4-1BB antibody or antigen binding fragment thereof comprises CDR3 of the variable domain of the heavy chain with a sequence identity of at least 50%, 60%, 70%, 80%, 85%, 90%, 91%, 92%, 93%, 94%, 95%, 96%, 97%, 98%, 99%, 99% or 100% with one of SEQ ID NO. 3, SEQ ID NO. 9, or SEQ ID NO. 15. In embodiments, CDR3 of the variable domain of the heavy chain of the anti-human OX40 antibody or antigen binding fragment thereof has a sequence identity of at least 50%, 60%, 70%, 80%, 85%, 90%, 91%, 92%, 93%, 94%, 95%, 96%, 97%, 98%, 99%, 99% or 100% with one of SEQ ID NO. 21, SEQ ID NO. 27, SEQ ID NO.33, SEQ ID NO. 39, SEQ ID NO. 45, SEQ ID NO. 51 or SEQ ID NO. 57.

Preferably, the antibodies are the specific antibodies described in greater detail herein.

A beneficial effect, as referred to herein, means that the immunostimulatory activity of the combined administration of antibodies, whether simultaneous, simultaneous separate or sequential, is greater than the activity resulting from the administration of a single antibody in at least one way. For example, administration of both antibodies may enhance the anti-tumour T-cell activity in a subject more than increased dosage or longer-term administration of a single antibody.

Anti-tumour T-cell activity can for example be measured in terms of increased T-cell activation in any suitable T-cell activity test, such as a PBMC proliferation assay, or by measuring attenuation in tumour growth, or reduction in tumour size.

4-1BB Antibodies 4-1BB is a receptor responsible for T-cell costimulation, as described above. Hence, 4-1BB agonist antibodies provide increased T-cell activation by increasing stimulation thereof through the 4-1BB receptor. A 4-1BB antibody can stimulate the 4-1BB receptor by mimicking the 4-1BB ligand, or otherwise binding to the 4-1BB receptor in a manner that mimics ligand binding.

We have found that antibodies active in promoting T-cell activation through agonising the 4-1BB receptor bind to domain 1 of the receptor. Thus, the invention provides antibodies which preferentially bind to domain 1 of 4-1BB.

Although the antibodies provided herein share light chain CDR sequences and heavy chain CDR1 and CDR2 sequences with known antibodies, the heavy chain CDR3 sequences are unique. It is known that heavy chain CDR3 retains primary responsibility for the specificity of antigen binding in antibodies. The CDR H3 sequences of the present invention may be combined with CDRs L1-L3 and H1-H2 with different primary sequences to those set forth herein, as long as the main chain conformation of the CDRs remains the same.

The invention therefore provides a 4-1BB agonist antibody having the heavy chain CDR3 sequences set forth in SEQ ID Nos 3, 9 or 15. Preferably, the antibody has a heavy chain CDR3 with the sequence of SEQ ID No. 15.

In embodiments, the antibody of the invention comprises light chain CDRs having the sequences set forth in SEQ ID Nos 4, 5 and 6; or SEQ ID Nos 10, 11 and 12; or SEQ ID Nos 16, 16 and 18.

In embodiments, the antibody of the invention comprises heavy chain CDRs having the sequences set forth in SEQ ID Nos 1, 2 and 3; or SEQ ID Nos 7, 8 and 9; or SEQ ID Nos 13, 14 and 15.

For example, the antibody can have the CDR sequences set forth herein in respect of clones SAP 1.3, SAP 3.14 or SAP 3.28, in SEQ ID Nos 1-18.

The sequences of the CDR regions may vary by a certain amount from those set forth in the SEQ IDs. Preferably, the sequences are at least 70% identical to the SEQ IDs. In embodiments, the sequences are at least 95% identical to the SEQ IDs, such as 96%, 97%, 98%, 99% or 100% identical.

OX40 Antibodies

OX40 is a receptor found on CD4 and CD8 T-cells, and is involved in activating maintaining the T-cell response, as set forth herein. Accordingly, an OX40 agonist antibody is useful for potentiating an immune response. Conversely, an OX40 antagonist is useful in inhibiting an unwanted or inappropriate immune response, such as an autoimmune response or an inflammatory response.

We have found that antibodies active in promoting T-cell activation though agonising the OX40 receptor bind to domain 3 or domain 4 of the receptor.

Although the antibodies provided herein share light chain CDR sequences and heavy chain CDR1 and CDR2 sequences with known antibodies, the heavy chain CDR3 sequences are unique. It is known that heavy chain CDR3 retains primary responsibility for the specificity of antigen binding in antibodies. The CDR H3 sequences of the present invention may be combined with CDRs L1-L3 and H1-H2 with different primary sequences to those set forth herein, as long as the main chain conformation of the CDRs remains the same.

The invention therefore provides OX40 agonist antibody having the heavy chain CDR3 sequences set forth in SEQ ID Nos 27, 45 or 57. There is moreover provided an OX40 antagonist antibody having the heavy chain CDR3 sequence set forth in SEQ ID No 39 or 51.

In a further embodiment, there is provided an OX40 antagonist antibody having the heavy chain CDR3 sequence set forth in SEQ ID No 39 or 51 in the context of an IgG1 isotype.

In embodiments, the antibody of the invention comprises light chain CDRs having the sequences set forth in SEQ ID Nos 22, 23 and 24; or SEQ ID Nos 28, 29 and 30; or SEQ ID Nos 34, 35 and 36; or SEQ ID Nos 40, 41 and 42; or SEQ ID Nos 46, 47 and 48; or SEQ ID Nos 52, 53 and 54; or SEQ ID Nos 58, 59 and 60.

In embodiments, the antibody of the invention comprises heavy chain CDRs having the sequences set forth in SEQ ID Nos 19, 20 and 21; or SEQ ID Nos 25, 26 and 27; or SEQ ID Nos 31, 32 and 33; or SEQ ID Nos 37, 38 and 39; or SEQ ID Nos 43, 44 and 45; or SEQ ID Nos 49, 50 and 51; or SEQ ID Nos 55, 56 and 57.

For example, the antibody can have the CDR sequences set forth herein in respect of clones SAP 28.2, SAP15.3, SAP 28.3, SAP9, SAP 25.29, SAP 29.23 or SAP 29.50, in SEQ ID Nos 19-60.

The sequences of the CDR regions may vary by a certain amount from those set forth in the SEQ IDs. Preferably, the sequences are at least 80% identical to the SEQ IDs. In embodiments, the sequences are at least 95% identical to the SEQ IDs, such as 96%, 97%, 98%, 99% or 100% identical.

The antibodies of the invention are preferably humanised, by transplanting the CDR sequences set forth above into a human framework. Human frameworks can be selected according to known techniques in the art, as discussed below.

Humanisation

Humanised forms of non-human (e.g., murine) antibodies are chimeric antibodies that contain minimal sequence derived from non-human immunoglobulin. For the most part, humanised antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Some or all of the CDRs of the antibodies described herein may be transferred; for example, it is possible to retain human acceptor CDRs as long as the donor CDR H3 is transferred. The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) J. Mol. Biol., 196: 901; Chothia et al. (1989) Nature, 342: 877). Analysis of loop lengths and key residues has therefore enabled prediction of the mainchain conformations of H1, H2, L1, L2 and L3 found in the majority of human antibodies (Chothia et al. (1992) J. Mol. Biol., 227: 799; Tomlinson et al. (1995) EMBO J., 14: 4628; Williams et al. (1996) J. Mol. Biol., 264: 220).

Advantageously, CDRs selected for use in combination with the H3 CDRs of the present invention have the same main chain conformation as those of the antibodies of the invention described herein.

Preferably, the antibodies according to the invention comprise an Fc region and are of the IgG1 or IgG2 isotype. Antibody fragments which retain the antigen-binding properties of full length antibodies may also be used, as set forth above. The human IgG2 isotype has been shown to be more effective than human IgG1, and the retention of the IgG2 hinge region is preferred (White et al, *Cancer Immunol Immunother.* 2013 May; 62(5):941-8 FcγRIIB controls the potency of agonistic anti-TNFR mAbs. White et al *J Immunol.* 2011 Aug. 15; 187(4):1754-63 Interaction with FcγRIIB is critical for the agonistic activity of anti-CD40 monoclonal antibody.) For a range of immunostimulatory antibodies in vivo and in vitro, whether stimulating a T-cell response (anti-hOX40, -h4-1BB, anti-m4-1BB, -hCD27, -hCD28, -hCD40-mCD40, -mCTLA4) or a B-cell response (anti-hCD40, -mCD40) the m1 isotype is active whereas m2a is inactive or less active.

Tumour Therapy

A tumour is a population of cells, or mass of tissue that forms in a subject as a result of the abnormal proliferation of malignant cancer cells. Tumours may result from any type of cancer and especially sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer, multiple myeloma and cerebral cancer.

In some embodiments, the cancer may be pancreatic cancer, for example pancreatic ductal adenocarcinoma (PDA).

Tumour therapy, as referred to herein, includes therapies which reduce the rate of tumour growth, that is slow down, but do not necessarily eliminate, tumour growth.

Reduction in the rate of tumour growth can be, for example, a reduction in at least 10%, 20%, 30%, 40%, 50%, 75%, 100%, 150%, 200% or more of the rate of growth of a tumour. For example, the rate of growth can be measured over 1, 2, 3, 4, 5, 6 or 7 days, or for longer periods of one or more weeks.

In some embodiments, the invention may result in the arrest of tumour growth, or the reduction in tumour size or the elimination of a tumour.

Cancer cells within the tumour in the subject may be immunologically distinct from normal somatic cells in the subject (for example, the tumour may be immunogenic; alternatively, even if it is not immunogenic, it may present different immunological determinants(s) from somatic cells). For example, the cancer cells may be capable of eliciting a systemic immune response in the subject against one or more antigens expressed by the cancer cells. The antigens that elicit the immune response may be tumour antigens or may be shared by normal cells.

In embodiments, the tumour, although presenting different antigenic determinants, is hidden from the immune system of a subject or is otherwise poorly targeted by T-cells. For example, the tumour may exclude immune cells, thus lowering its immunological visibility and/or preventing the immune system from acting to attack the tumour, or tumour-specific T cells may be insufficiently activated to mount an effective anti-tumour response.

Accordingly, the treatment of cancer as provided herein results in at least one of the following:

(i) promotion of T cell immune responses:

(ii) promotion of the generation of antigen-specific memory T cells;

(iii) promotion of the expansion T cells in an antigen-dependent manner;

(iv) promotion of Th1 immunity; and/or (v) promotion of the proliferation or survival of antigen-specific T cells including at least one of naive or non naive CD8+ T cells, CD8+ effector cells, or memory cells, or T cells which optionally may be genetically engineered that have been expanded in vitro and then transferred to humans.

CD8+ T cells that are specific for cancer cells within the cancerous tumour may be present in the subject.

In embodiments, CD8+ T cells are absent from the cancerous tumour or are absent from regions of the tumour that contain cancer cells. In some embodiments, the cancer cells may express one or more antigens that are not expressed by normal somatic cells in the subject (i.e. tumour antigens). Tumour antigens are known in the art and may elicit immune responses in the subject. In particular, tumour antigens may elicit T cell-mediated immune responses against cancer cells in the subject i.e. the tumour antigens may be recognized by CD8+ T cells in the subject.

Tumour antigens expressed by cancer cells in a cancerous tumour may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE and immunogenic fragments thereof (Simpson et al., Nature Rev (2005) 5, 615-625, Gure et al., Clin Cancer Res (2005) 11, 8055-8062; Velazquez et al., Cancer Immun (2007) 7, 1 1; Andrade et al., Cancer Immun (2008) 8, 2; Tinguely et al., Cancer Science (2008); Napoletano et al., Am J of Obstet Gyn (2008) 198, 99 e91-97).

Other tumour antigens that may be expressed include, for example, overexpressed or mutated proteins and differentiation antigens particularly melanocyte differentiation antigens such as p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomeras, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29/BCAA), CA 195, CA 242, CA-50, CAM43, CD68/KP1, CO-029, FGF-5, G250, Ga733 (EpCAM), HTgp-175, M344, MA-50, MG7-Ag, MOV18, NB/170K, NY-CO-1, RCAS1, SDCCAG16, TA-90 (Mac-2 binding protein/cyclophilin C-associated protein), TAAL6, TAG72, TLP, and TPS and tyrosinase related proteins such as TRP-1, TRP-2.

Other tumour antigens that may be expressed include out-of-frame peptide-MHC complexes generated by the non-AUG translation initiation mechanisms employed by "stressed" cancer cells (Malarkannan et al. Immunity 1999).

Other tumour antigens that may be expressed are well-known in the art (see for example WO00/20581; Cancer Vaccines and Immunotherapy (2000) Eds Stern, Beverley and Carroll, Cambridge University Press, Cambridge) The sequences of these tumour antigens are readily available from public databases but are also found in WO 1992/020356 A1, WO 1994/005304 A1, WO 1994/023031 A1, WO 1995/020974 A1, WO 1995/023874 A1 and WO 1996/026214 A1.

A subject suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

In some embodiments, the subject is a human. In other embodiments, non-human mammals, especially mammals that are conventionally used as models for demonstrating therapeutic efficacy in humans (e.g. murine, primate, porcine, canine, or rabbit animals) may be employed.

In some embodiments, the subject may have minimal residual disease (MRD) after an initial cancer treatment.

A subject with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in a subject may include identification of a particular cell type (e.g. a cancer cell) in a sample of a body fluid or tissue obtained from the subject.

An anti-cancer compound may be any anti-cancer drug or medicament which has activity against cancer cells. Suitable anti-cancer compounds for use in combination with the antibodies as disclosed herein may include aspirin, sulindac, curcumin, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); thylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics, such as actimomycin D, daunomycin (rubidomycin), doxorubicin, mitoxantrone, idarubicin, bleomycins, plicamycin (mithramycin), mitomycinC, and actinomycin; enzymes such as L-asparaginase, cytokines such as interferon (IFN)-gamma, tumour necrosis factor (TNF)-alpha, TNF-beta and GM-CSF, anti-angiogenic factors, such as angiostatin and endostatin, inhibitors of FGF or VEGF such as soluble forms of receptors for angiogenic factors, including soluble VGF/VEGF receptors, platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors and receptor tyrosin kinase inhibitors such as imatinib mesylate (marketed as Gleevac or Glivac) and erlotinib (an EGF receptor inhibitor) now marketed as Tarveca; and anti-virals such as oseltamivir phosphate, Amphotericin B, and palivizumab.

While it is possible anti-OX40 or anti-4-1-BB antibodies and anti-cancer compounds to be administered alone, it is preferable to present the compounds in the same or separate pharmaceutical compositions, formulated with pharmaceutically acceptable components as appropriate.

A pharmaceutical composition may comprise, in addition to the antibody and/or an anti-cancer compound, one or more pharmaceutically acceptable carriers, adjuvants, excipients, diluents, fillers, buffers, stabilizers, preservatives, lubricants, or other materials well known to those skilled in the art. Suitable materials will be sterile and pyrogen-free, with a suitable isotonicity and stability. Examples include sterile saline (e.g. 0.9% NaCl), water, dextrose, glycerol, ethanol or the like or combinations thereof. Such materials should be non-toxic and should not interfere with the efficacy of the active compound. The precise nature of the carrier or other material will depend on the route of administration, which may be by bolus, infusion, injection or any other suitable route, as discussed below. Suitable materials will be sterile and pyrogen free, with a suitable isotonicity and stability. Examples include sterile saline (e.g. 0.9% NaCl), water, dextrose, glycerol, ethanol or the like or combinations thereof. The composition may further contain auxiliary substances such as wetting agents, emulsifying agents, pH buffering agents or the like.

Suitable carriers, excipients, etc. can be found in standard pharmaceutical texts, for example, Remington's Pharmaceutical Sciences, 18th edition, Mack Publishing Company, Easton, Pa., 1990.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

In some embodiments, one or both of the antibodies may be provided in a lyophilized form for reconstitution prior to administration. For example, lyophilized reagents may be re-constituted in sterile water and mixed with saline prior to administration to a subject.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Optionally, other therapeutic or prophylactic agents may be included in a pharmaceutical composition or formulation.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a subject susceptible to or at risk of the occurrence or re-occurrence of cancer may be treated as described herein. Such treatment may prevent or delay the occurrence or re-occurrence of cancer in the subject.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of cytolytic T-lymphocytes, and a decrease in levels of tumour-specific antigens. Reducing immune suppression in cancerous tumours in a subject may improve the capacity of the subject to resist cancer growth, in particular growth of a cancer already present the subject and/or decrease the propensity for cancer growth in the subject.

Antibodies may be administered as described herein in therapeutically-effective amounts.

The term "therapeutically-effective amount" as used herein, pertains to that amount of an active compound, or a combination, material, composition or dosage form comprising an active compound, which is effective for producing some desired therapeutic effect, commensurate with a reasonable benefit/risk ratio.

It will be appreciated that appropriate dosages of the active compounds can vary from patient to patient. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the patient. The amount of active compounds and route of administration will ultimately be at the discretion of the physician, although generally the dosage will be to achieve concentrations of the active compound at a site of therapy without causing substantial harmful or deleterious side-effects.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

Administration of anti-cancer compounds and the antibodies of the invention may be simultaneous, separate or sequential. By "simultaneous" administration, it is meant that the anti-cancer compounds and the antibodies of the invention are administered to the subject in a single dose by the same route of administration.

By "separate" administration", it is meant that the anti-cancer compounds and the antibodies of the invention are administered to the subject by two different routes of administration which occur at the same time. This may occur for example where one agent is administered by infusion or parenterally and the other is given orally during the course of the infusion or parenteral administration.

By "sequential" it is meant that the anti-cancer compounds and the antibodies of the invention are administered at different points in time, provided that the activity of the first administered agent is present and ongoing in the subject at the time the second agent is administered. For example, the anti-cancer compounds may be administered first, such that an immune response against a tumour antigen is generated, followed by administration of the antibody, such that immune action at the site of the tumour is enhanced, or vice versa.

Preferably, a sequential dose will occur such that the second of the two agents is administered within 48 hours, preferably within 24 hours, such as within 12, 6, 4, 2 or 1 hour(s) of the first agent.

The same principles can be applied to simultaneous, separate or sequential administration of the antibodies of the invention.

Multiple doses of antibody may be administered, for example 2, 3, 4, 5 or more than 5 doses may be administered.

Likewise, multiple doses of anti-cancer compound may be administered over a period of time.

Multiple doses of the anti-cancer compounds may be administered, for example 2, 3, 4, 5 or more than 5 doses may be administered. The administration of the anti-cancer compounds may continue for sustained periods of time. For example treatment with the anti-cancer compounds may be continued for at least 1 week, at least 2 weeks, at least 3 weeks, at least 1 month or at least 2 months. Treatment with the anti-cancer compounds may be continued for as long as is necessary to achieve complete tumour rejection.

The active compounds or pharmaceutical compositions comprising the active compounds may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Usually administration will be by the intravenous route, although other routes such as intraperitoneal, subcutaneous, transdermal, oral, nasal, intramuscular or other convenient routes are not excluded.

The pharmaceutical compositions comprising the active compounds may be formulated in suitable dosage unit formulations appropriate for the intended route of administration.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions may be prepared in the form of a concentrate for subsequent dilution, or may be in the form of divided doses ready for administration. Alternatively, the reagents may be provided separately within a kit, for mixing prior to administration to a human or animal subject.

In some embodiments, the treatment of a subject using an antibody as described herein may further comprise administering one or more immunotherapeutic agents to the subject.

An immunotherapeutic agent may facilitate or enhance the targeting of cancer cells by the immune system, in particular T cells, through the recognition of antigens expressed by the cancer cells.

Suitable agents include adoptive T cell therapies and cancer vaccine preparations designed to induce T lymphocytes (T cells) recognizing a localized region of an antigen or epitope specific to the tumour cell.

A cancer vaccine is an agent, a cell-based agent, molecule, or immunogen which stimulates or elicits an endogenous immune response in a subject or subject against one or more tumour antigens. Suitable cancer vaccines are known in the art and may be produced by any convenient technique.

The use of tumour antigens to generate immune responses is well-established in the art (see for example; Kakimi K, et al. Int J Cancer. 2011 Feb. 3; Kawada J, Int J Cancer. 2011 Mar. 16; Gnjatic S, et al. Clin Cancer Res. 2009 Mar. 15; 15(6):2130-9; Yuan J, et al. Proc Natl Acad Sci USA. 2008 Dec. 23; 105(51):20410-5; Sharma P, et al. J Immunother. 2008 Nov.-Dec.; 31(9):849-57; Wada H, et al. Int J Cancer. 2008 Nov. 15; 123(10):2362-9; Diefenbach C S, et al. Clin Cancer Res. 2008 May 1; 14(9):2740-8; Bender A, et al. Cancer Immun. 2007 Oct. 19; 7:16; Odunsi K, et al. Proc Natl Acad Sci USA. 2007 Jul. 31; 104(31):12837-42; Valmori D, et al. Proc Natl Acad Sci USA. 2007 May 22; 104(21):8947-52; Uenaka A, et al. Cancer Immun. 2007 Apr. 19; 7:9; Kawabata R, et al. Int J Cancer. 2007 May 15; 120(10):2178-84; Jäger E, et al. Proc Natl Acad Sci USA. 2006 Sep. 26; 103(39):14453-8; Davis I D Proc Natl Acad Sci USA. 2005 Jul. 5; 102(27):9734; Chen Q, Proc Natl Acad Sci USA. 2004 Jun. 22; 101(25):9363-8; Jäger E, Proc Natl Acad Sci USA. 2000 Oct. 24; 97(22):12198-203; Carrasco J, et al. J Immunol. 2008 Mar. 1; 180(5):3585-93; van Baren N, et al. J Clin Oncol. 2005 Dec. 10; 23(35): 9008-21; Kruit W H, et al. Int J Cancer. 2005 Nov. 20; 117(4):596-604; Marchand M, et al. Eur J Cancer. 2003 January; 39(1):70-7; Marchand M et al. Int J Cancer. 1999

Jan. 18; 80(2):219-30; Atanackovic D, et al. Proc Natl Acad Sci USA. 2008 Feb. 5; 105(5):1650-5).

Cancer cells from the subject may be analyzed to identify a tumour antigen expressed by the cancer cells. For example, a method as described herein may comprise the step of identifying a tumour antigen which is displayed by one or more cancer cells in a sample obtained from the subject. A cancer vaccine comprising one or more epitopes of the identified tumour antigen may then be administered to the subject whose cancer cells express the antigen. The vaccine may induce or increase an immune response, preferably a T cell mediated immune response, in the subject against the cancer cells expressing the identified tumour antigen.

The cancer vaccine may be administered before, at the same time, or after the antibodies are administered to the subject as described herein.

Adoptive T cell therapy involves the administration to a subject of tumour-specific T cells to a subject. Preferably, the T cells were previously isolated from the subject and expanded ex vivo. Suitable adoptive T cell therapies are well known in the art (J. Clin Invest. 2007 Jun. 1; 117(6): 1466-1476.)

Immunotherapeutic agents also include other immunomodulatory antibodies, such as antibodies which target immunological checkpoints. Examples include antibodies specific for CTLA4, PD1 and PDL1.

In embodiments, the anti-OX40 or 4-1BB antibodies of the invention are coadminstered with anti-PD1 antibodies. We have shown that anti-OX40 antibody SAP25-29 is synergistic with anti-PD1 in the treatment of AML.

Therefore, the invention provides an OX40 agonist and an anti-PD1 checkpoint inhibitor antibody for use in treating AML.

The antibodies of the invention may also be coadministered with antibodies specific for CD27, as provided for in our European patent application EP 2 083 858.

Immunoactive agents and therapeutic agents which can be coadministered with the antibodies of the invention thus include:
 (i) an anti-CD70 antibody,
 (ii) an anti-B7.1 antibody,
 (iii) an anti-B7.2 antibody,
 (iv) an anti-CTLA-4 antibody,
 (v) an anti-CD28 antibody,
 (vi) a moiety that depletes or blocks regulatory T cells,
 (vii) a cytokine,
 (viii) a chemotherapeutic,
 (ix) a radiotherapeutic,
 (x) an immunomodulator,
 (xi) an immunostimulant,
 (xii) immune stimulatory antibody or protein that acts as a positive costimulant,
 (xiii) an immune antibody or protein that acts as a negative costimulant,
 (xiv) an antibody or other moiety that blocks inhibitory signals to T cells, and
 (xv) an antibody that binds to tumor cells or vasculature or stroma.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Identity

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

The invention is further described below, with reference to the following examples.

EXAMPLES

Example 1: Development of Agonist OX40 Antibodies

Twenty three clones were screened for effect on PBMC proliferation obtained from several healthy donors (FIGS. 1A and B).

Based on these in vitro results and on in vivo results (Examples 4 and 5 below), three antibodies were selected for humanization: SAP29-50, SAP25-29, and SAP29-23.

These antibodies seem to bind to Domains 3 and/or 4 of OX40 (FIG. 1C).

SAP9 also binds to domains 3 and/or 4, but unlike SAP29-50, SAP29-23 and SAP25-29, its binding to OX40 is blocked by OX40L (FIG. 2).

SAP 28.2 is the only antibody found to bind domain 1 (FIG. 1C)

SAP15.3 and SAP28.3 both bind to domain 2 (FIG. 1C).

BLAST-patent sequence analysis shows that the heavy chain CDR3 sequence of all three humanized antibodies is unique (Table 1).

All three antibodies retain binding activity once humanized (FIGS. 3 A, B, and C).

TABLE 1

| Clone | Chain | Region | Sequence | Similarity | SEQ ID |
|---|---|---|---|---|---|
| SAP28.2 | Vh | CDR1 | GFSLTSYGVH | 100% | 19 |
|  |  | CDR2 | VIWAGGSTNYNSALMS | 100% | 20 |
|  |  | CDR3 | VREDDPY | 86% | 21 |
|  | Vk | CDR1 | RASQDISNYLN | 100% | 22 |
|  |  | CDR2 | YTSRLHS | 100% | 23 |
|  |  | CDR3 | QQGNTLPF | 100% | 24 |
| SAP15.3 | Vh | CDR1 | GFTFSSSYIS | 100% | 25 |
|  |  | CDR2 | WIYAGTGGTSYNQKFTG | 94% | 26 |
|  |  | CDR3 | ARHDYDWFAY | 70% | 27 |
|  | Vk | CDR1 | RASSSVSSSYLH | 100% | 28 |
|  |  | CDR2 | STSNLAS | 100% | 29 |
|  |  | CDR3 | QQYSGYPYT | 100% | 30 |
| SAP28.3 | Vh | CDR1 | GFSLSTSGKGVT | 92% | 31 |
|  |  | CDR2 | TIWWDDDNRYNPSLKS | 100% | 32 |
|  |  | CDR3 | VQSDWDGAMDY | 63% | 33 |
|  | Vl | CDR1 | RASSSVSYIH | 100% | 34 |
|  |  | CDR2 | ATSNLAS | 100% | 35 |
|  |  | CDR3 | QQWSSHPT | 87% | 36 |
| SAP9 | Vh | CDR1 | GFSLSTSGLGVT | 91% | 37 |
|  |  | CDR2 | LIYWDDDKRYHPSLKS | 94% | 38 |
|  |  | CDR3 | ARRALGTFDY | 70% | 39 |

TABLE 1-continued

| Clone | Chain | Region | Sequence | Similarity | SEQ ID |
|---|---|---|---|---|---|
| | Vk | CDR1 | RASQDISHYLN | 100% | 40 |
| | | CDR2 | YTSRLHS | 100% | 41 |
| | | CDR3 | QQGHTLPPT | 100% | 42 |
| SAP25.29 | Vh | CDR1 | SYIMH | 100% | 43 |
| | | CDR2 | YINPYNDNTKNNEKFKG | 88% | 44 |
| | | CDR3 | MDYGDYPYFDY | 81% | 45 |
| | Vk | CDR1 | RASQDISNYLN | 100% | 46 |
| | | CDR2 | YTSRLHS | 100% | 47 |
| | | CDR3 | QQGNTLPFT | 100% | 48 |
| SAP29.23 | Vh | CDR1 | DHYMY | 100% | 49 |
| | | CDR2 | TISDGGRHTYYPDSVKG | 88% | 50 |
| | | CDR3 | DLGKALDY | 88% | 51 |
| | Vk | CDR1 | RASENIYSNLA | 100% | 52 |
| | | CDR2 | AATNLAD | 100% | 53 |
| | | CDR3 | QHFWGTPWT | 100% | 54 |
| SAP29.50 | Vh | CDR1 | RYIMQ | 100% | 55 |
| | | CDR2 | YINPYNDGTRYNEKFKG | 100% | 56 |
| | | CDR3 | FGFGDYLYFDY | 54% | 57 |
| | Vk | CDR1 | RASQDIRNYLN | 100% | 58 |
| | | CDR2 | YTSRLHS | 100% | 59 |
| | | CDR3 | QQGNTLPYT | 100% | 60 |

Example 2: Development of Agonist 4-1BB Antibodies

Twenty clones were screened for their effect on PBMC (peripheral blood mononucleated cells) T-cell proliferation obtained from several healthy donors. 3 clones that resulted in a consistent increase in proliferation of at least 2-fold were selected: SAP1-3, SAP3-14 and SAP3-28 (FIGS. 8A and B).

These three clones seem to bind to Domain 1 of 4-1BB (FIG. 8C).

The three selected clones were humanized. BLAST-patent sequence analysis shows that the heavy chain CDR3 sequence of all three humanized antibodies is unique (Table 2).

Humanized clone SAP3-14 was very poorly secreted and could not be further investigated. Binding of the remaining two clones to 4-1BB immobilised on Biacore chip was compared to the parent antibodies. Only humanized clone SAP3-28 retained binding (FIG. 9).

Example 3: Anti-4-1BB and Anti-OX40 Antibodies of the mIgG2a Isotype are Inhibitory All of the anti-4-1BB antibodies from the original fusions were of the mIgG1 isotype. All but two of the original anti-OX40 antibodies were mIgG1; the two exceptions were SAP9 and SAP29-23.

SAP9 and SAP29-23 were inhibitory in in vitro T-cell proliferation assays (FIG. 4). The mIgG1 variants of both mAbs, however, were found to be stimulatory.

mIgG2a variants of anti-4-1BB antibodies were also found to be inhibitory in in vitro T-cell proliferation assays (FIG. 10).

A similar difference in the activity of mIgG1 and mIgG2a versions of the anti-OX40 antibodies was also observed in in vivo models (Example 5 below).

TABLE 2

| Clone | Chain | Region | Sequence | Similarity | SEQ ID |
|---|---|---|---|---|---|
| SAP1.3 | Vh | CDR1 | SYGVH | 100% | 1 |
| | | CDR2 | VIWSGGIT | 100% | 2 |
| | | CDR3 | NGRIGSTMTLYYAMDY | 50% | 3 |
| | Vk | CDR1 | RSSKSLLHSNGITYLY | 100% | 4 |
| | | CDR2 | QMSNLAS | 100% | 5 |
| | | CDR3 | AQNLELPLT | 100% | 6 |
| SAP3.14 | Vh | CDR1 | NYGVH | 100% | 7 |
| | | CDR2 | VIWSGGST | 100% | 8 |
| | | CDR3 | NPYYRVFMDY | 62% | 9 |
| | Vk | CDR1 | RASESVDSYGNSFMH | 100% | 10 |
| | | CDR2 | RASNLES | 100% | 11 |
| | | CDR3 | QQSNEDPFT | 100% | 12 |
| SAP3.28 | Vh | CDR1 | SYGVH | 100% | 13 |
| | | CDR2 | VIWRGGST | 100% | 14 |
| | | CDR3 | PLGTSWDAMDY | 66% | 15 |
| | Vk | CDR1 | RASQDISNYLN | 100% | 16 |
| | | CDR2 | YKSRLHS | 86% | 17 |
| | | CDR3 | QQGNTLPYT | 100% | 18 |

Example 4: Human OX40 Knock-in Mice hOX40 knock-in (KI) mice were produced for us by Ozgene.

FIG. 5 shows a comparison of the expression of mOX40 and hOX40 on splenic T cells following activation with anti-CD3 and anti-CD28. hOX40 is expressed on both CD4 and CD8 cells at a low level prior to activation, whereas mOX40 is not. The pattern of hOX40 expression on CD4 cells following activation was similar to that of mOX40 (FIG. 5A). On CD8 cells, whereas there is only a transient/low expression of mOX40 following activation, the expression of hOX40 is greater and more prolonged (FIG. 5B).

The expression of hOX40 on regulatory T cells is somewhat lower than mOX40 (FIG. 5C).

Heterozygous hOX40 KIs mice have been crossed with OT-1 mice and splenocytes from these, which express both hOX40 and mOX40, used in adoptive transfer experiments.

Example 5: Activity of Anti-hOX40 Antibodies In Vivo

In Example 2 we have shown that antibodies from our anti-hOX40 panel are agonistic as mIgG1 reagents and able to stimulate CD4 and CD8 T-cell responses.

Here we show that these antibodies are also active in an in vivo anti-OVA OT-1 adoptive transfer model (FIG. 6) using OT-1 cells expressing both human and mouse OX40.

Importantly, each of the anti-hOX40 antibodies induced a level of stimulation of anti-OVA T-cells that was comparable with an anti-mOX40 antibody, OX86, but with slightly slower initial expansion of the OT-1 cells (FIG. 6). So far 10 of the panel have been shown to be stimulatory (FIG. 6C).

Seven of these clones bind to domains 3 and/or 4 of OX40, two bind to domain 2 and one binds to domain 1 (FIGS. 1A and C).

As observed in vitro (Example 1, FIG. 4), anti-OX40 antibodies of the m2a isotype, whether these are the parent antibodies from the original fusions (SAP9 and SAP29-23) or engineered variants (SAP25-29 and SAP29-50), are inactive or inhibitory.

The humanised SAP25-29 and SAP29-23 anti-hOX40 antibodies (linked to mIgG1 constant regions) that retained their binding activity (FIG. 3) gave a similar level of stimulation to the parent antibodies (FIG. 6D).

Clone SAP25-29 was shown to be efficacious in combination with an anti-PD1 antibody in the C1498 mouse model of AML (FIG. 7).

Example 5—Combination of Anti-OX40 and Anti-4-1BB Antibodies

In in vitro assays, a combination of an anti-4-1BB (SAP3-28) antibody and an anti-OX40 antibody (SAP25-29) was shown to stimulate a significantly higher level of stimulation than with either of the antibodies alone (FIG. 11).

---

The invention claimed is:

1. An isolated monoclonal antibody which specifically binds to the cysteine rich repeat sequences in one or more of the extracellular domains 3 or 4 of OX40 comprising a:
   (a) heavy chain CDRs comprising SEQ ID NO: 37-39 and light chain CDRs comprising SEQ ID NO: 40-42;
   (b) heavy chain CDRs comprising SEQ ID NO: 43-45 and light chain CDRs comprising SEQ ID NO: 46-48;
   (c) heavy chain CDRs comprising SEQ ID NO: 49-51 and light chain CDRs comprising SEQ ID NO: 52-54; or
   (d) heavy chain CDRs comprising SEQ ID NO: 55-56 and light chain CDRs comprising SEQ ID NO: 58-60.

2. The isolated monoclonal antibody according to claim 1 wherein the Fc region of the antibody is derived from either the mouse IgG1 or human IgG2 isotype.

3. The isolated monoclonal antibody according to claim 2, wherein the antibody is of hIgG2 isotype.

4. The isolated monoclonal antibody according to claim 1 comprising heavy chain CDRs having SEQ ID NO: 37-39 and light chain CDRs having SEQ ID NO: 40-42.

* * * * *